US011559397B2

(12) United States Patent
Metcalf et al.

(10) Patent No.: US 11,559,397 B2
(45) Date of Patent: Jan. 24, 2023

(54) HEART VALVE REPAIR

(71) Applicant: Medtronic Vascular, Inc., Santa Rosa, CA (US)

(72) Inventors: Olivia Metcalf, Santa Rosa, CA (US); Matthew E. Genovese, Windsor, CA (US); Caitlin Dorff, Santa Rosa, CA (US); Emily Grimm, Petaluma, CA (US); Fatemeh Fatemi Far, Santa Rosa, CA (US); Karan Punga, San Rafael, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 192 days.

(21) Appl. No.: 16/710,898

(22) Filed: Dec. 11, 2019

(65) Prior Publication Data
US 2020/0188092 A1 Jun. 18, 2020

Related U.S. Application Data

(60) Provisional application No. 62/779,302, filed on Dec. 13, 2018.

(51) Int. Cl.
*A61F 2/24* (2006.01)

(52) U.S. Cl.
CPC ............ *A61F 2/243* (2013.01); *A61F 2/2436* (2013.01); *A61F 2/2445* (2013.01)

(58) Field of Classification Search
CPC ...... A61F 2/243; A61F 2/2436; A61F 2/2445; A61F 2220/0016; A61F 2220/0091; A61F 2250/001; A61F 2/2466
See application file for complete search history.

(56) References Cited

U.S. PATENT DOCUMENTS 8,574,289 B2 * 11/2013 Cartledge ............ A61F 2/2433
623/2.11
2011/0166649 A1 7/2011 Gross et al.
2011/0208295 A1 * 8/2011 Cartledge ............ A61F 2/2466
623/2.11

(Continued)

FOREIGN PATENT DOCUMENTS

WO 2008/097999 A2 8/2008
WO 2018109329 A1 6/2018

OTHER PUBLICATIONS

International Search Report and Written Opinion of International Application No. PCT/US2019/065840, dated Mar. 12, 2020, 9 pp.

(Continued)

*Primary Examiner* — Jacqueline Woznicki
(74) *Attorney, Agent, or Firm* — Medler Ferro Woodhouse & Mills PLLC

(57) ABSTRACT

In some examples, a delivery device includes a handle that includes a control member, an elongate body, a plurality of arms extending from a distal portion of the elongate body to a distal collar configured to releasably couple to an annuloplasty device. The plurality of arms is operatively coupled to the control member and configured to position the annuloplasty device at a target site in a patient. The delivery device further comprises a plurality of anchors configured to secure the annuloplasty device to tissue at the target site, each respective anchor of the plurality of anchors deployable from a respective arm of the plurality of arms.

16 Claims, 19 Drawing Sheets

(56) References Cited

U.S. PATENT DOCUMENTS

| | | | |
|---|---|---|---|
| 2011/0301701 A1 | 12/2011 | Padala et al. | |
| 2013/0226289 A1* | 8/2013 | Shaolian | A61F 2/2448 623/2.37 |
| 2013/0331930 A1 | 12/2013 | Rowe et al. | |
| 2016/0038285 A1* | 2/2016 | Glenn | A61F 2/2466 623/2.11 |
| 2016/0045312 A1 | 2/2016 | Braido et al. | |
| 2020/0100898 A1* | 4/2020 | Vola | A61F 2/2445 |

OTHER PUBLICATIONS

Extended European Search Report, EP Application No. 19894644.4, dated Jul. 19, 2022.

* cited by examiner

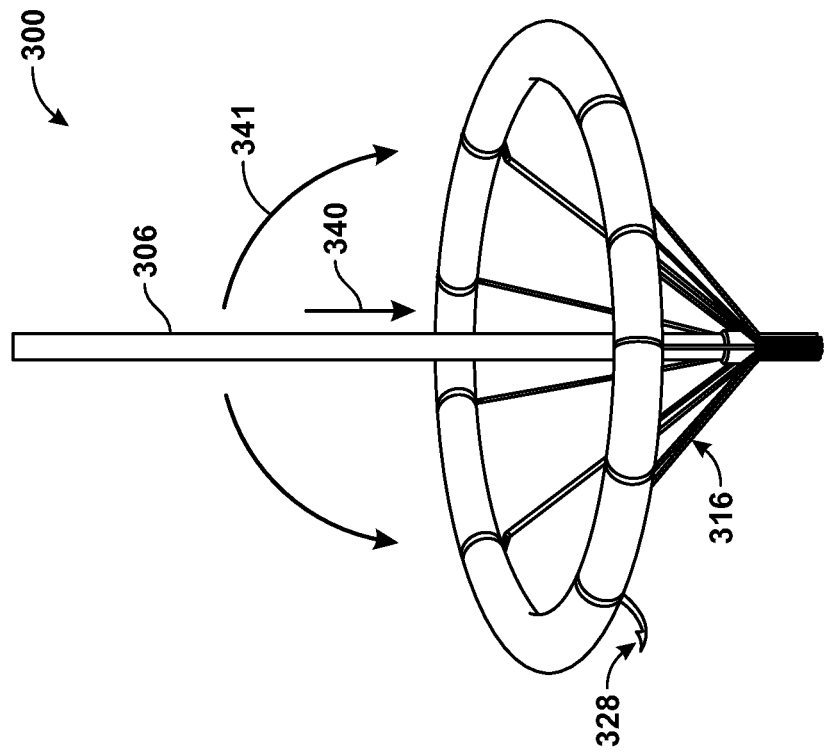
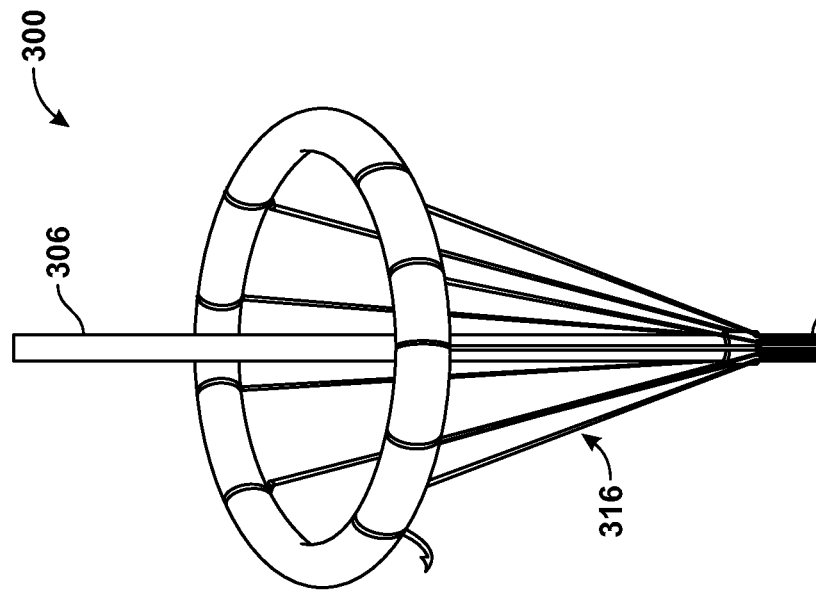
FIG. 3D
FIG. 3C

HEART VALVE REPAIR

This application claims the benefit of U.S. Provisional Patent Application Ser. No. 62/779,302, filed on Dec. 13, 2018, the entire content of which is incorporated by reference herein.

TECHNICAL FIELD

This disclosure relates to heart valve repair, such as mitral valve repair.

BACKGROUND

Some patient conditions can produce valvular insufficiency or regurgitation in a heart of the patient. Valvular insufficiency or regurgitation occurs when a valve in a heart of a subject does not close completely, allowing blood to flow backwards (e.g., from the left ventricle to the left atrium), which may adversely impact the functionality of the heart.

The mitral valve includes two leaflets (anterior and posterior) attached to an annulus (e.g., a fibrous ring). In a healthy heart, the mitral valve leaflets close during contraction of the left ventricle and prevent blood from flowing back into the left atrium. Mitral valve regurgitation is a condition in which the leaflets of a mitral valve of a subject do not coapt properly and, as a result, blood regurgitates back into the left atrium from the left ventricle. The regurgitation of blood back into the left atrium may result in a reduced ejection volume from the left ventricle, causing the heart of the subject to work relatively hard to supply the desirable volume of blood to the body. Mitral regurgitation may occur because of different patient conditions. For example, secondary mitral regurgitation, also referred to as functional mitral regurgitation, may occur when a left ventricle dilates and causes dilation of the mitral annulus of a subject.

SUMMARY

The present disclosure describes devices, systems, and techniques for repairing a heart valve, such as, but not limited to, a mitral valve. The devices, systems, and techniques described herein may be used to treat mitral valve regurgitation or other patient conditions that involve valves. In some examples, an annuloplasty device is configured to reduce spacing between valve leaflets, which may improve coaptation of the valve leaflets and may help reduce valvular insufficiency or regurgitation. Examples of delivery devices for delivering such an annuloplasty device are described herein.

In some aspects, this disclosure describes example delivery devices including a handle that includes a control member, an elongate body, a plurality of arms extending from a distal portion of the elongate body to a distal collar configured to releasably couple to an annuloplasty device, where the plurality of arms is operatively coupled to the control member and configured to position the annuloplasty device at a target site in a patient, and a plurality of anchors configured to secure the annuloplasty device to tissue at the target site, each respective anchor of the plurality of anchors deployable from a respective arm of the plurality of arms.

In some aspects, this disclosure describes example medical system that includes an annuloplasty device and a delivery device configured to deliver the annuloplasty device to a target site in a patient. The delivery device may include a handle that includes a control member, an elongate body extending along a longitudinal axis from a proximal end coupled to the handle to a distal portion, a plurality of arms extending from the distal portion of the elongate body to a distal collar configured to releasably couple to the annuloplasty device, where the plurality of arms is operatively coupled to the control member and configured to position the annuloplasty device at the target site, and a plurality of anchors configured to secure the annuloplasty device to tissue at the target site, each respective anchor of the plurality of anchors deployable from a respective arm of the plurality of arms.

The details of one or more examples are set forth in the accompanying drawings and the description below. Other features, objects, and advantages will be apparent from the description and drawings, and from the claims.

BRIEF DESCRIPTION OF DRAWINGS

FIGS. 3A-3I are conceptual diagrams illustrating an example annuloplasty device and an example delivery device configured to deliver the annuloplasty device, the delivery device including a plurality of rigid arms.

DETAILED DESCRIPTION

This disclosure describes, systems, and techniques for repairing a heart valve, such as, but not limited to, a mitral valve. In some cases, treatment of valve regurgitation may include valve repair by reshaping or reinforcing portions of a valve, such as the valve leaflets or valve annulus, to improve valve coaption. For example, an annuloplasty device (e.g., an annuloplasty ring) may be implanted on or near the valve annulus and used to draw the annulus into a smaller configuration, bringing the valve leaflets closer together, and allowing improved closure during ventricular contraction. For example, the annuloplasty device may be configured to exert the radially inward force on tissue of the valve annulus or proximate to the valve annulus in order to urge the valve leaflets toward each other to help improve coaptation of the valve leaflets.

Annuloplasty devices (e.g., annuloplasty rings) may be relatively rigid, relatively flexible, or a combination having both rigid and flexible segments. Rigid annuloplasty rings may cause the valve annulus to be rigid and unable to flex in response to the contractions of the ventricle, thus inhibiting the natural, three-dimensional movement of the valve.

Flexible annuloplasty rings may include a fabric that is sewn to the annular ring with a line of sutures. The sutures may result in formation of scar tissue and loss of flexibility of the mitral valve. Combination annuloplasty rings may be sutured in place and result in formation of scar tissue and loss of mitral valve flexibility. The devices, systems, and techniques described herein may be used to treat valve regurgitation using a relatively flexible annuloplasty device that is inserted into the coronary sinus and adapts to the shape of the coronary sinus. Using example delivery devices described herein, the annuloplasty band may be manipulated to a reduced diameter and/or radius of curvature, which reduces the diameter and/or radius of curvature of the coronary sinus. In this way, a circumference of the mitral annulus may be reduced, which may urge the valve leaflets toward each other and improve coaptation of the valve leaflets.

Figure 1A:
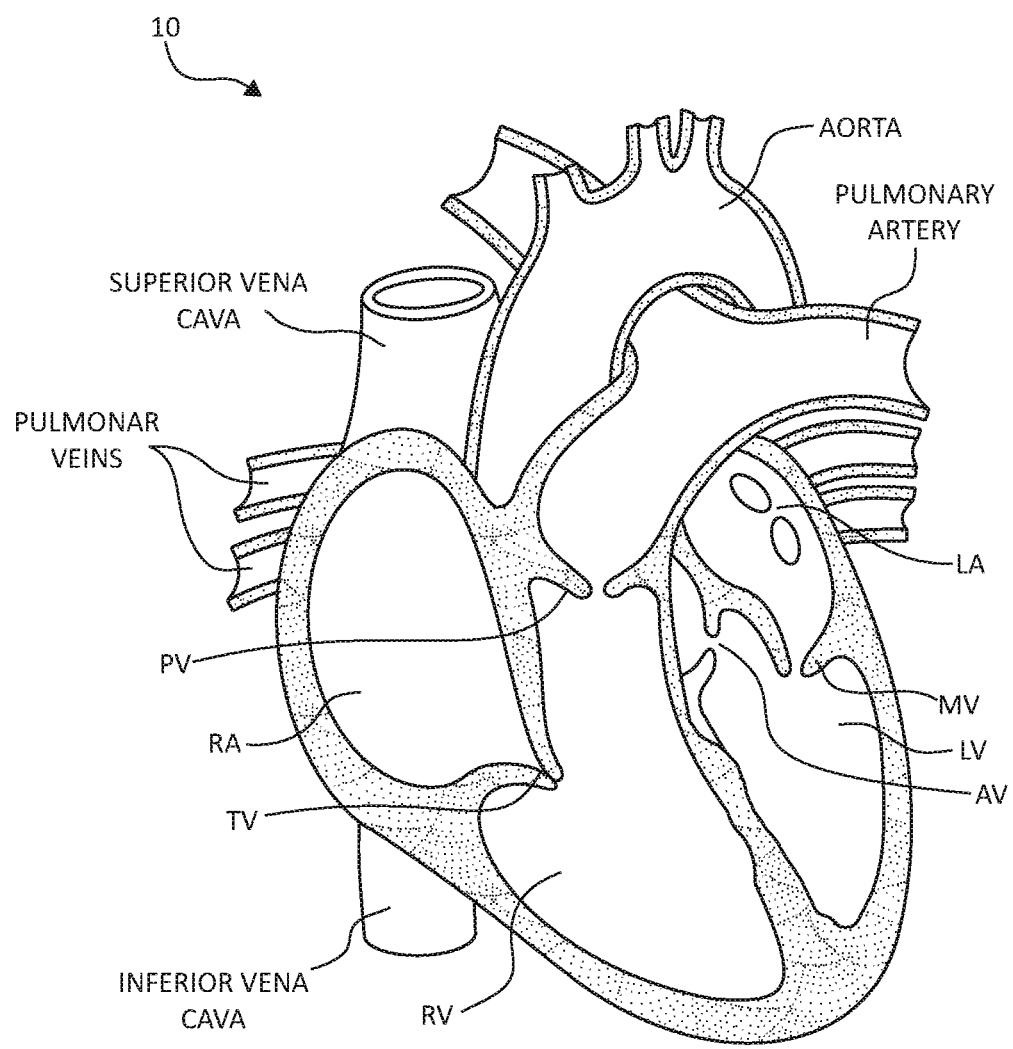
FIGS. 1A and 1B are schematic cross-sectional views of an example human heart.
Figure 1B:
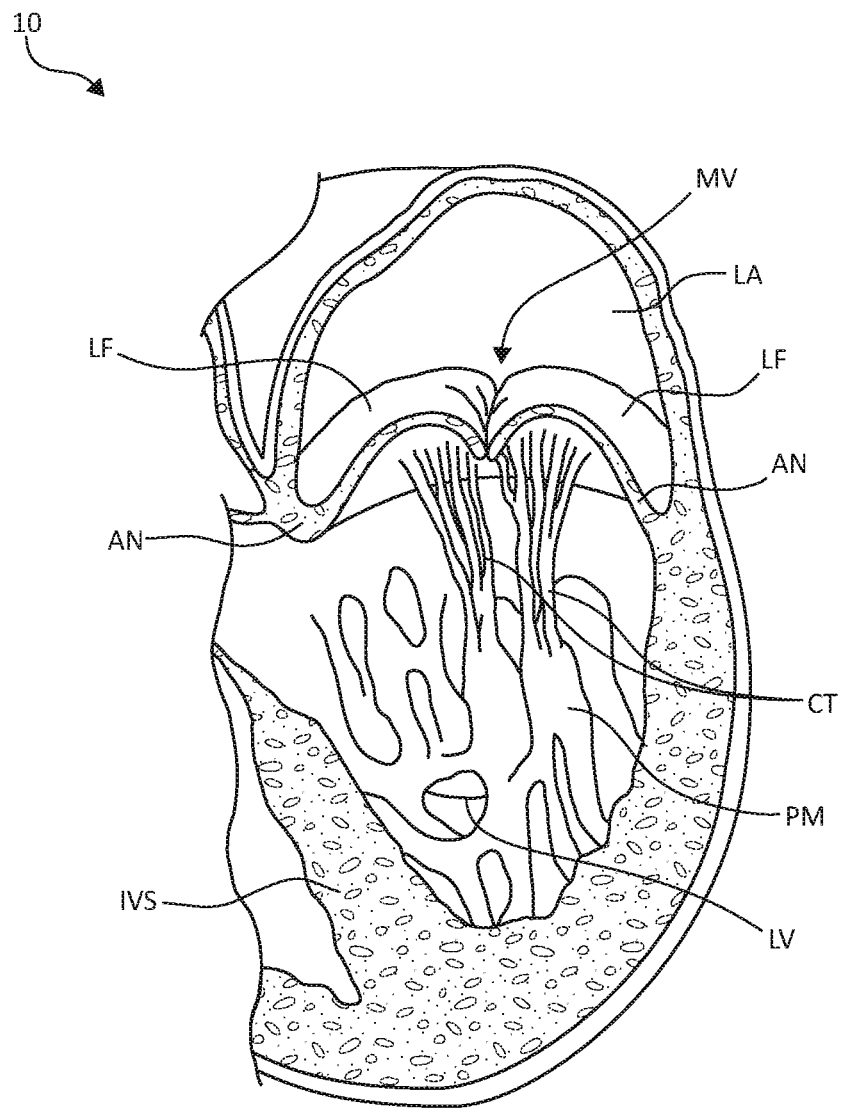

FIGS. 1A and 1B are schematic cross-sectional views of an example human heart 10. The human heart 10 is a four chambered, muscular organ that provides blood circulation through the body during a cardiac cycle. The four main chambers include the right atrium (RA) and right ventricle (RV) which supplies the pulmonary circulation, and the left atrium (LA) and left ventricle (LV) which supplies oxygenated blood received from the lungs to the remaining body. To ensure that blood flows in one direction through the heart, atrioventricular valves (tricuspid valve (TV) and mitral valves (MV)) are present between the junctions of the atrium and the ventricles, and semi-lunar valves (pulmonary valve (PV) and aortic valve (AV)) govern the exits of the ventricles leading to the lungs and the rest of the body. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendineae CT.

Mitral valve regurgitation is a condition in which the leaflets of a mitral valve of a subject do not coapt properly and, as a result, blood regurgitates back into the left atrium LA from the left ventricle LV. The regurgitation of blood back into the left atrium LA may result in a reduced ejection volume from the left ventricle LV, causing the heart of the subject to work relatively hard to supply the desirable volume of blood to the body. Mitral regurgitation may occur because of one or more patient conditions. For example, secondary mitral regurgitation, also referred to as functional mitral regurgitation, may occur when the left ventricle LV dilates and causes dilation of the mitral annulus of a patient. The leaflets LF of the valves may move apart as a result of the dilation of the left ventricle LV, which may adversely impact the ability of the leaflets to properly coapt.

In addition to or instead of being caused by dilation of the left ventricle LV, mitral valve regurgitation (or other valve regurgitation) may be caused by calcified plaque buildup in heart 10. For example, the leaflets LF of the valves (e.g., aortic valve AV or mitral valve MV) may harden and may not sufficiently coapt or meet, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated.

The medical devices, systems, and techniques described herein may be used to repair a valve of heart 10 via a minimally invasive medical procedure, e.g., via a transcatheter, trans-septal medical procedure that is less invasive than open heart surgery. While open heart surgeries, such as annuloplasty performed via open heart surgery, may have positive outcomes, a more minimally invasive medical procedure may also have positive outcomes while also being associated with a shorter recovery time for some patients compared to open heart surgery.

Figure 2:
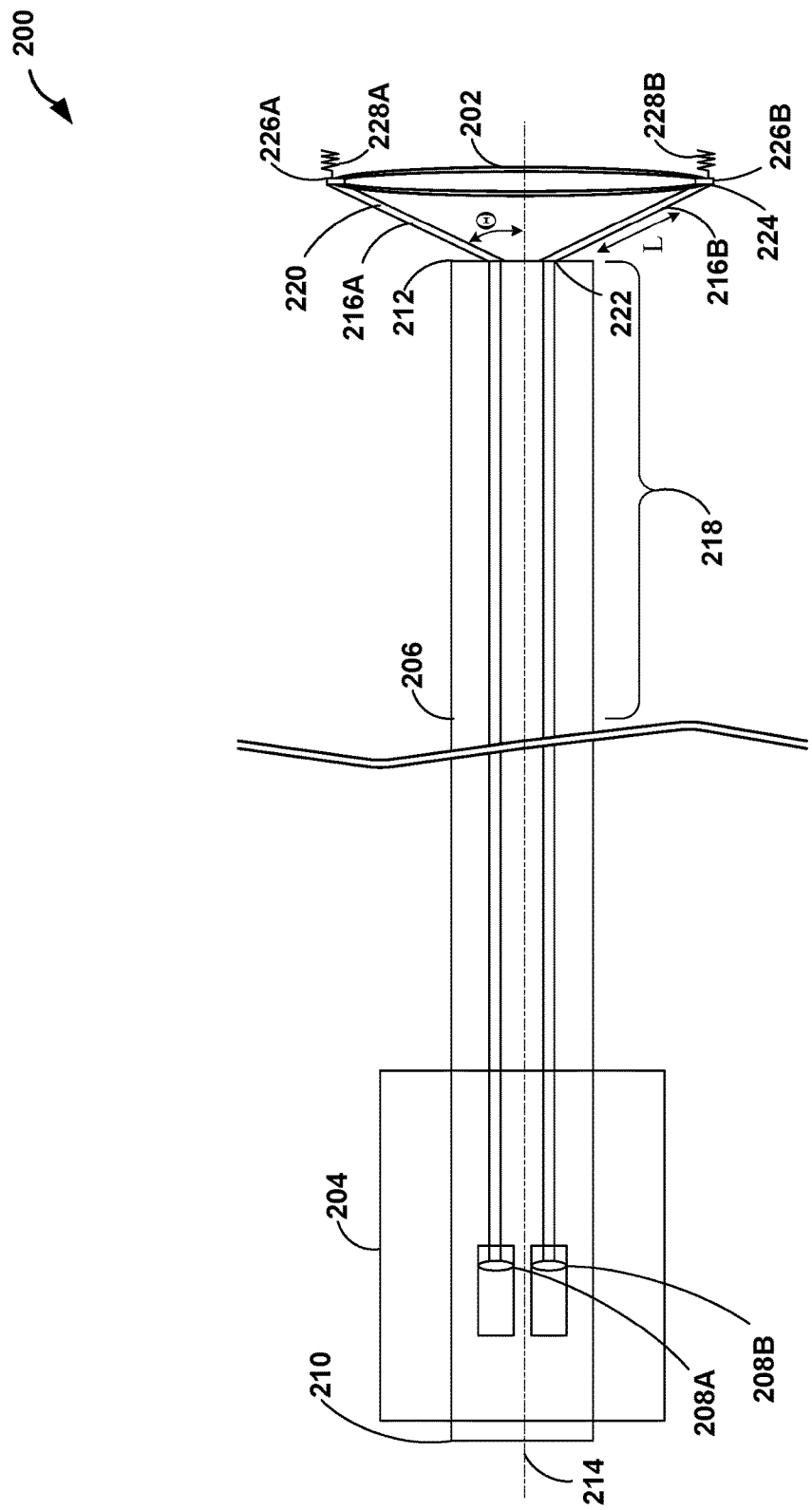
FIG. 2 is a conceptual diagram illustrating an example delivery device configured to deliver and secure an annuloplasty device to a heart valve.

FIG. 2 is a conceptual diagram illustrating an example delivery device 200 configured to deliver and secure an annuloplasty device 202 to a valve of heart 10. Annuloplasty device 202 can be, for example, an annuloplasty ring, partial ring, or any other suitable annuloplasty device configured to urge the valve leaflets toward each other. Delivery device 200 may include a handle 204 and an elongate body 206. Handle 204 includes control members 208A and 208B (collectively, "control member 208"). In some examples, handle 204 may include fewer control members, such as one control member, or more control members, such as eight control members.

Elongate body 206 defines one or more lumens extending from proximate a proximal end 210 to proximate a distal end 212 (e.g., from proximal end 210 to distal end 212) along a longitudinal axis 214. Proximal end 210 may be coupled to handle 204. For example, at least a portion of proximal end 210 may be mechanically attached or adhered to at least a portion of handle 204. Distal end 212 may define one or more apertures corresponding to the one or more lumens. Elongate body 206 can include, for example, a catheter. Elongate body 206 may include any suitable materials, such as, for example, one or more layers of medical grade polymers. In some examples, elongate body 206 may include one or more metal wire coils configured to improve transfer for a force, such as a push or pull force along longitudinal axis 214 or a torque about longitudinal axis 214.

Delivery device 200 includes a plurality of arms 216A and 216B (collectively, "arms 216"). Although illustrated as including two arms 216, in some examples, delivery device 200 may include more arms 216, such as between three arms and eight arms, or more. Arms 216 maybe controllable, e.g., by control member 208, between an retracted configuration (not shown) and an extended configuration (as shown in FIG. 2). Arms 216 assume a lower profile in the retracted configuration relative to the extended configuration. In some examples, in the retracted configuration, arms 216 may be positioned at least partially within, such as entirely within, a lumen of elongate body 206 or a recess in distal portion 218 of elongate body 206. In some examples, in the extended configuration, arms 216 may extend from distal portion 218 of elongate body 206. In the extended configuration, each arm of arms 216 may extend from distal portion 218 a substantially similar length L or dissimilar lengths. In some examples, in the extended configuration, arms 216 may extend from distal portion 218 at an angle θ, relative to longitudinal axis 214. In the extended configuration, each arm of arms 216 may extend away from longitudinal axis 214 at a substantially similar angle or dissimilar angles.

In some examples, arms 216 may define a lumen 220 extending from a proximal end 222 of arms 216 to a distal end 224. Lumen 220 may be sized to allow passage therethrough of control wires and/or anchors. For example, each arm of arms 216 and/or a respective control wire associated a respective arm of arms 216 may be, independently or in combination with one or more different arms of arms 216 and/or control wires, operatively coupled to control member 208. In this way, control member 208 may be used to control a longitudinal position of arms 216 and/or control wires associated with arms 216. A clinician may position annuloplasty device 202 at a treatment site within a patient by at least controlling longitudinal position of arms 216 using delivery device 200.

In some examples, arms 216A and 216B extend from distal portion 218 of elongate body 206 to a respective distal collar 226A and 226B (collectively, "distal collars 226"). Distal collars 226 may be configured to releasably couple to annuloplasty device 202. For example, distal collars 226 may be mechanically coupled to respective arms 216 to delivery annuloplasty device 202 to a target site. After positioning at the target site, arms 216 may be controlled, e.g., via control wires, to release distal collars 226. In this way, medical device may deliver annuloplasty device 202 to a desired location.

In some examples, distal collars 226A and 226B may be coupled to respective anchors 228A and 228B (collectively, "anchors 228"). Anchors 228 may be configured to secure a portion of annuloplasty device 202 to tissue at the target site. In some examples, each respective anchor of anchors 228 may be individually deliverable from a respective arm of arms 216. For example, anchors 228 may include a shape memory alloy, such as a nickel titanium alloy, having a preformed shape, such as a helix or a hook. The preformed shape can be a pre-set shape toward which a respective anchor recovers in the absence of an applied force. Lumen 220 of arms 216 may be sized to retain anchors 228 in a deformed configuration, such as a substantially straight shape, to maintain anchors 228 in a lower profile configuration during delivery of annuloplasty device 202 and to help prevent premature engagement of anchors 228 with tissue of heart 10. Arms 216 may be configured to deploy anchors 228, e.g., via control wires, into tissue at the target site, such that anchors 228 engage the tissue and remain coupled to collars 226.

Figure 3A:
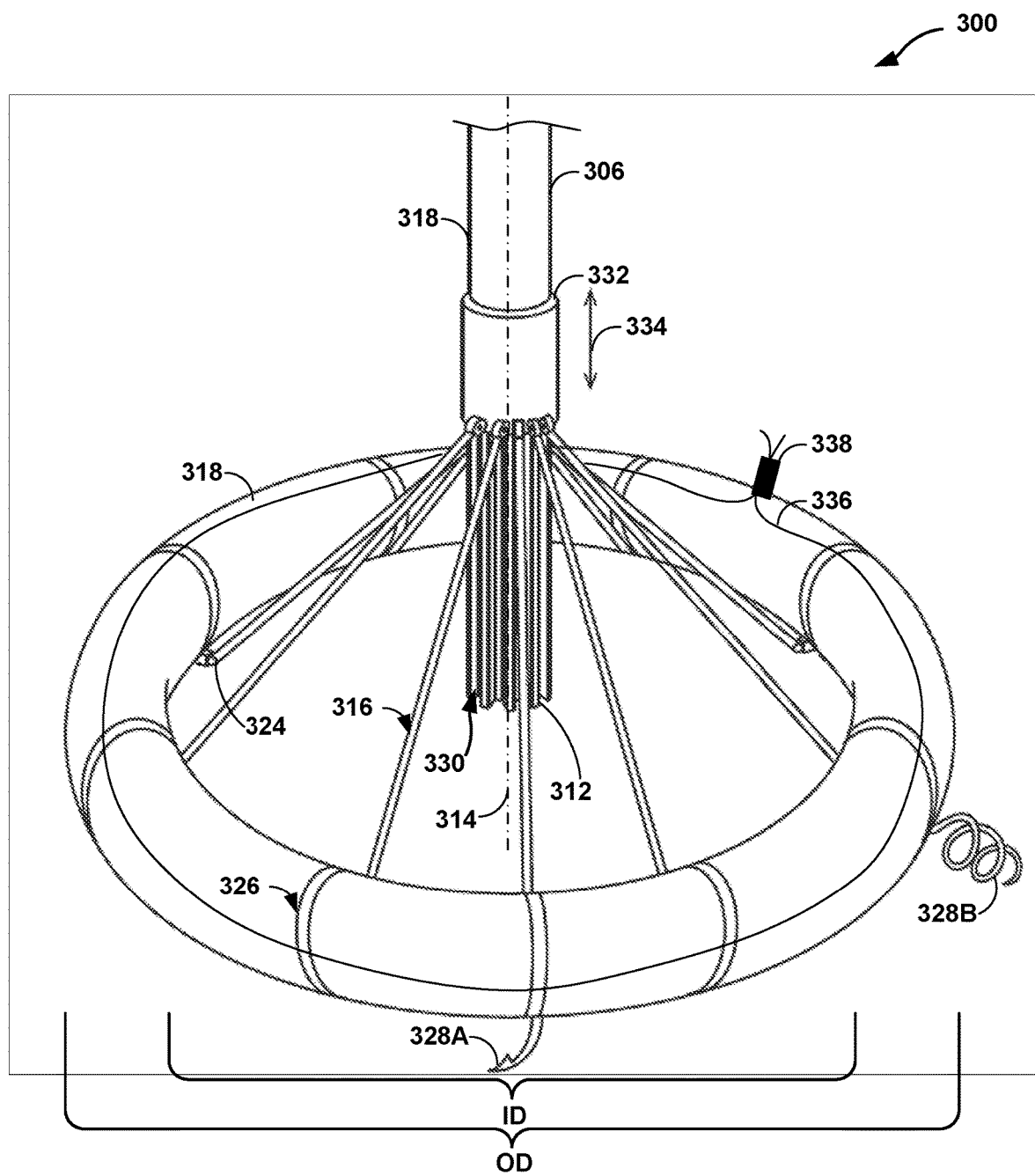

In some examples, arms 216 may be relatively rigid. For example, arms 216 may be relatively more rigid, for example, compared to annuloplasty device 202. FIGS. 3A-3I are conceptual diagrams illustrating an example delivery device 300 including a plurality of rigid arms 316A-316I (collectively, "arms 316"). Delivery device 300 may be the same as or substantially similar to delivery device 200 describe above in reference to FIG. 2 except for differences described below. Arms 316 may be relatively more rigid than annuloplasty device 302 to enable an expanded configuration of arms 316 to control a configuration (e.g., shape or size, such as a diameter or other cross-sectional dimension) of annuloplasty device 302. When arms 316 are in the expanded configuration, e.g., as shown in FIG. 3A, arms 316 may apply a radially outward or inward force to annuloplasty device 302 to control the configuration of annuloplasty device 302.

As illustrated in FIG. 3A, medical device 330 includes an elongate body 306 defining a distal portion 318 extending to a distal end 312. Arms 316 extend from a collar 332 slidably engaged with distal portion 318. For example, collar 332 may be controlled via a control member (e.g., control member 208A or 208B shown in FIG. 2) of a handle (not shown) to slide in two opposing directions as indicated by arrows 334.

Figure 3B:
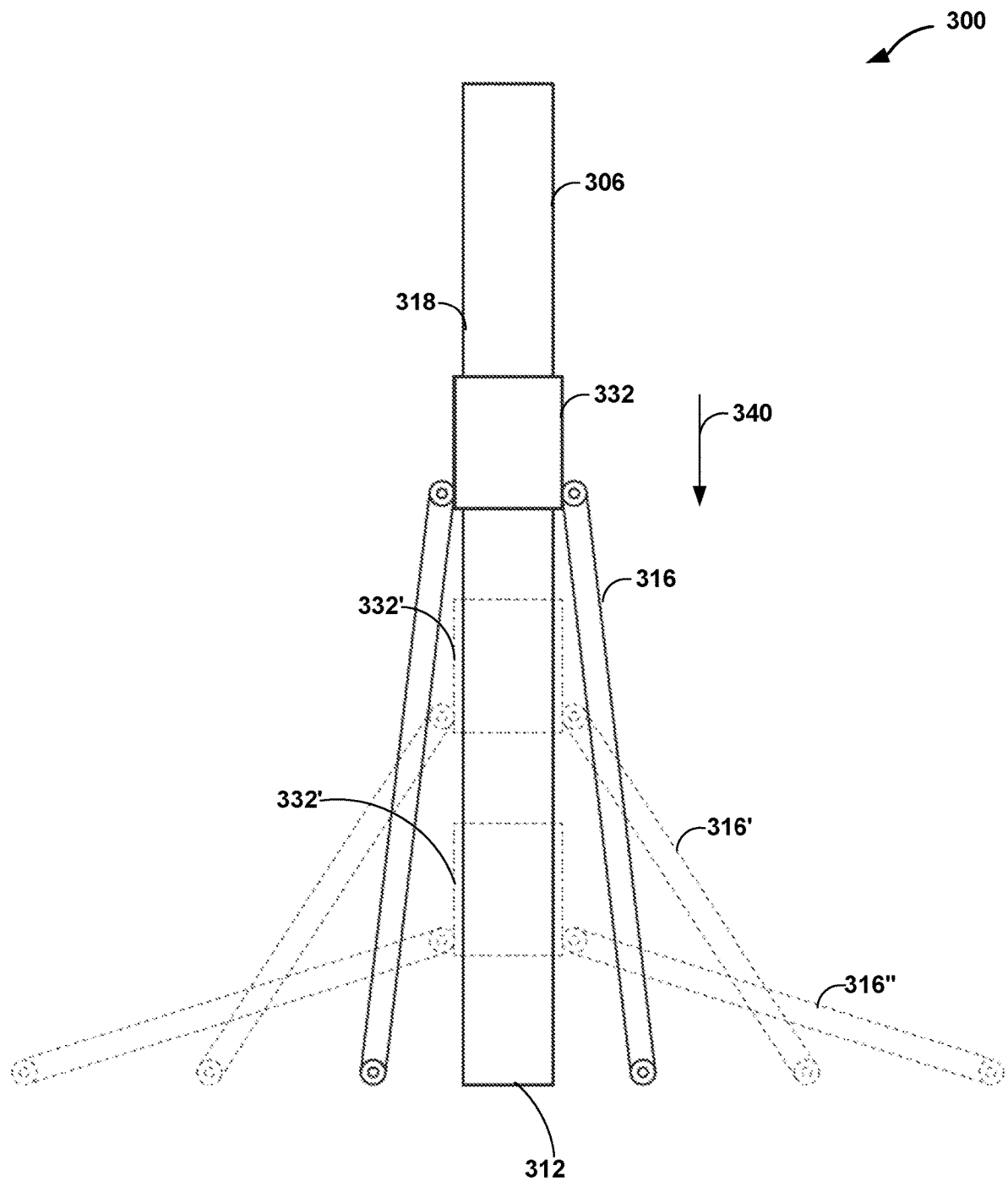
Figure 3F:
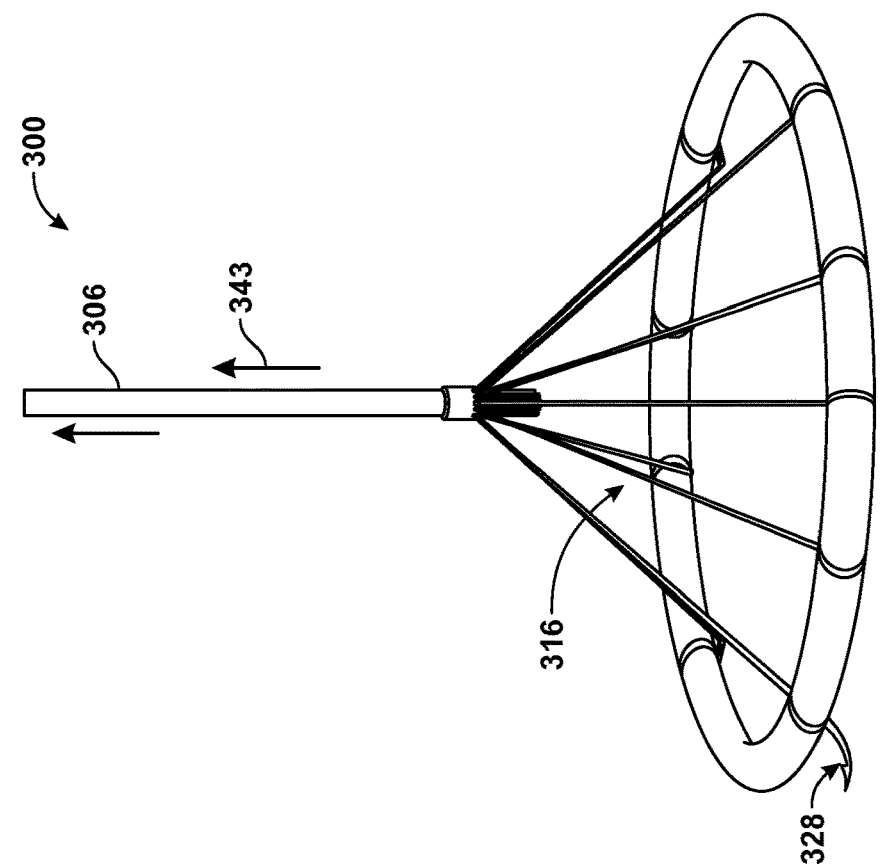

As illustrated in FIG. 3B, a retracted configuration of arms 316 may include a position of arms 316 that is lower profile compared to the expanded configuration, e.g., substantially parallel to elongate body 306. Substantially parallel may include parallel or within about 45-degrees of parallel, such as within about 20-degrees of parallel, or within about 10-degrees of parallel. As collar 332 is moved in a distal direction (e.g., in the direction of arrow 340), to an intermediate position (332') arms 316 may expand to an intermediate configuration (316') and, upon further movement of collar 332 to a final (e.g., distal-most) position (332") arms 316 may expand to an expanded configuration (316"), as indicated by the dashed lines.

Figure 3E:
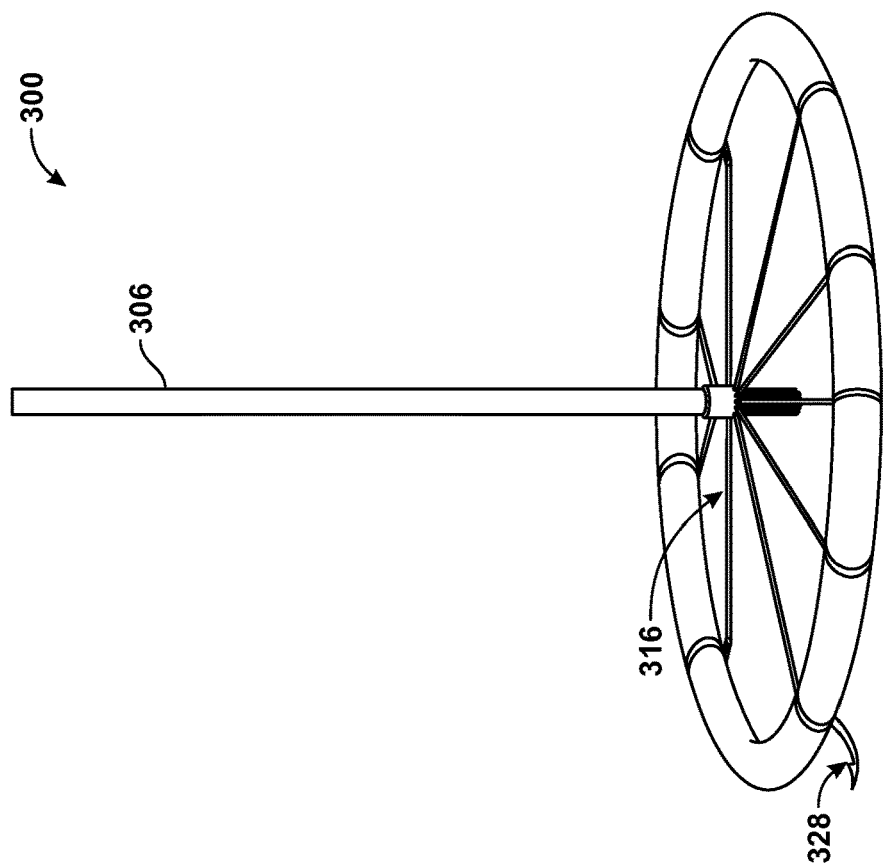

In some examples, rather than folding arms 316 toward distal end 312 of elongate body 306, arms 316 may fold in a proximal direction in the retracted configuration, as illustrated in FIG. 3C. As illustrated in FIG. 3D, in examples in which arms 316 fold in a proximal direction in the retracted configuration, as collar 332 is moved in a distal direction (e.g., in the direction of arrow 340) to an intermediate position, arms 316 may fold distally in the direction of arrows 341. When arms 316 reach a position substantially perpendicular to a longitudinal axis of elongate body 306, as illustrated in FIG. 3E, anchors 328 may be deployed to engage tissue at a target site. After anchors 328 are deployed to engage tissue at a target site, collar 332 may be moved in a proximal direction (e.g., in the direction of arrow 343 in FIG. 3F) to apply a radially inward force to tissue at the target site. The force applied to tissue at the target site may cause cinching of the tissue. For example, when the tissue of the target site includes the annulus of mitral valve MV, the cinching may cause a reduction in the diameter or circumference of the annulus of mitral valve MV.

Figure 3H:
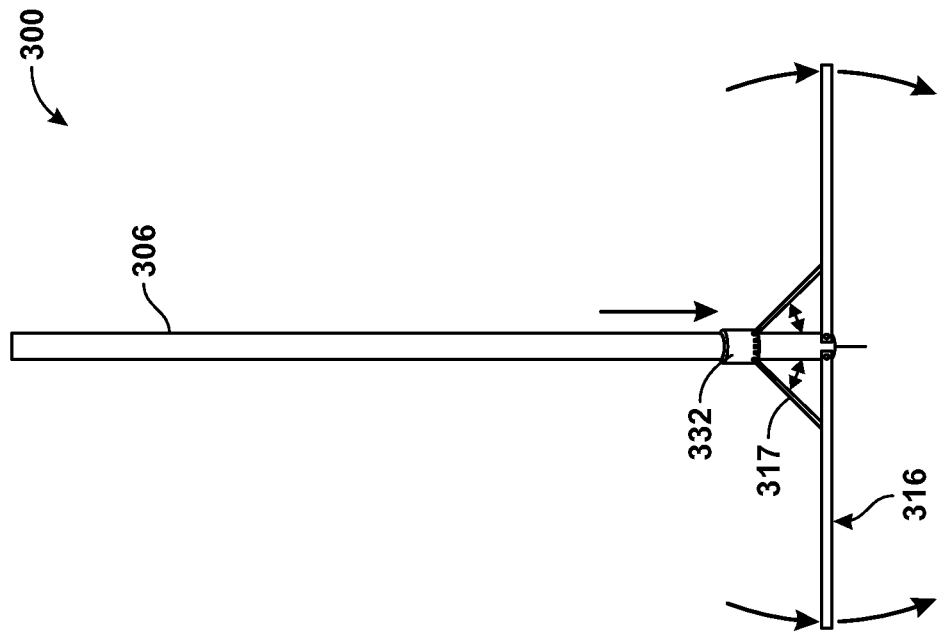
Figure 3G:
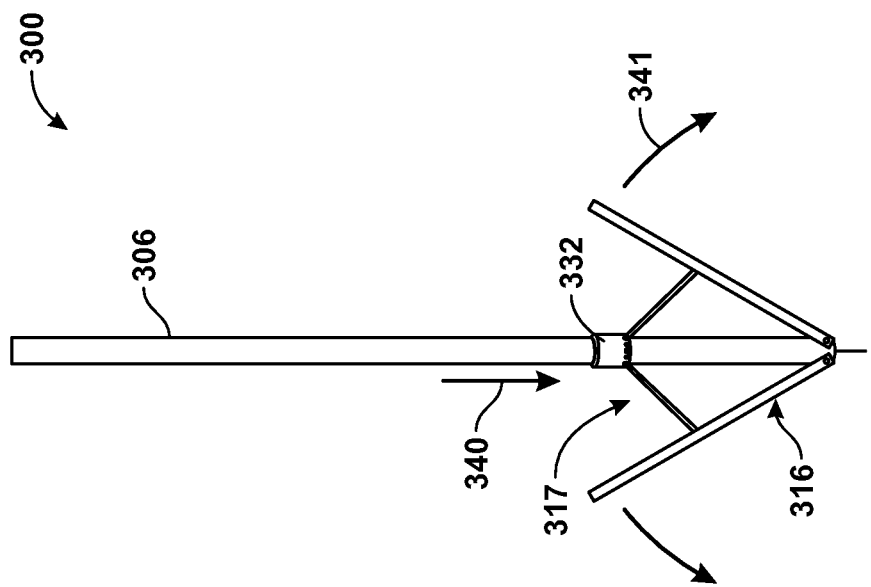
Figure 3I:
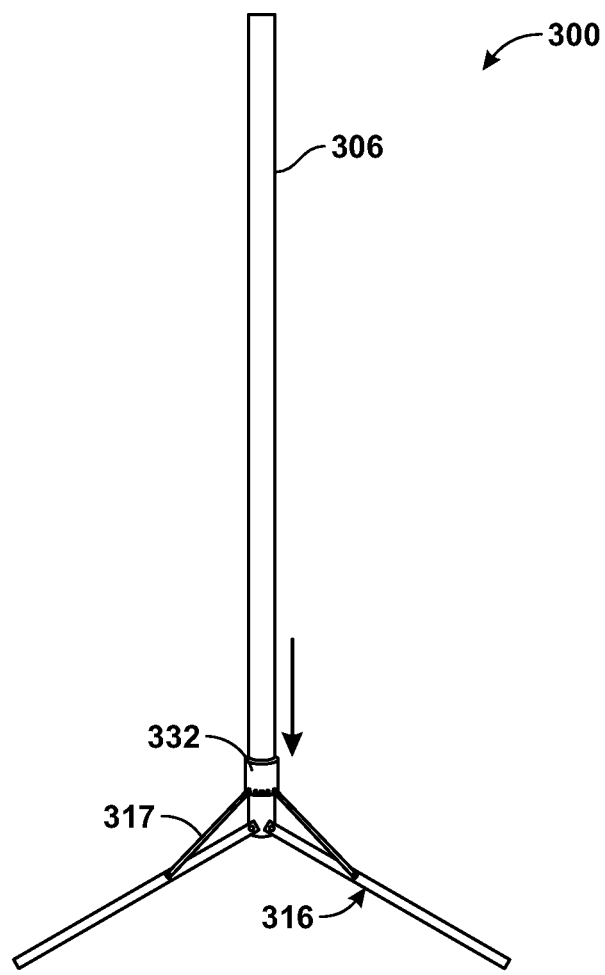

In some examples, as illustrated in FIG. 3G, arms 316 may include supports 317. Supports 317 are configured to stabilize and/or control the movement of arms 316 as arms 316 move from a retracted configuration to an expanded (deployed) configuration. For example, as collar 332 is moved in a distal direction (e.g., in the direction of arrow 340) to an intermediate position, supports 317 stabilize and/or control the movement of arms 316 as arms 316 fold distally in the direction of arrows 341. When arms 316 reach a position substantially perpendicular to a longitudinal axis of elongate body 306, as illustrated in FIG. 3H, supports 317 may prevent arms 316 from moving further in the distal direction. In this way, supports 317 may control the movement of arms 316 to expand to a fully expanded configuration, and not past the fully expanded configuration. For example, supports 317 may prevent arms 316 from moving past the fully expanded configuration into a configuration illustrated in FIG. 3I. In some examples, in the fully expanded configuration of arms 316, arms 316 may be less than perpendicular to a longitudinal axis of elongate body 306.

In some examples, as illustrated in FIG. 3A, distal portion 318 of elongate body 306 includes a plurality of recesses 330A-330I (collectively, "recesses 330"). Recesses 330 may be shaped to receive respective arms 316 in the retracted configuration. For example, each respective arm of arms 316 may nest within a respective recess of recesses 330 such that in the retracted configuration an outer surface of distal portion 318 of elongate body 336 is substantially smooth. A substantially smooth outer surface may include an outer surface profile that may be passed through a lumen, such as a lumen of a catheter or a vessel of a patient, without interfering with or abrading the lumen.

In the retracted configuration, annuloplasty device 302 may be in a collapsed shape. For example, annuloplasty device 302 may include a relatively flexible material compared to arms 316. The relatively flexible material may enable annuloplasty device 302 to be folded and/or compressed into the collapsed shape. The collapsed shape of annuloplasty device 302 may allow annuloplasty device 302 to be loaded into lumen of a delivery catheter, e.g., such as a lumen of distal portion 318 of elongate body 306. In some examples, collapsed annuloplasty device 302 may be deployable from distal end 312 of elongate body 316.

In some examples, after deployment of annuloplasty device 302, collar 332 may be controlled to move arms 316 into the expanded configuration of arms 316, as illustrated in FIG. 3A. In some examples, annuloplasty device 302 may include a shape-memory alloy structure (e.g., a wire-frame structure in the shape of a ring or partial ring) configured to, upon deployment, automatically unfold and/or expand into the expanded configuration of annuloplasty device 302, as shown in FIG. 3A. In some examples, annuloplasty device 302 may include an expandable structure similar to an expandable stent. In addition to or instead of being configured to self-expand, annuloplasty device 302 may include structure configured to, in response to a force, such as via an inflatable balloon, unfold and/or expand into the expanded configuration of annuloplasty device 302. In the expanded configuration of annuloplasty device 302, annuloplasty device 302 may be relatively more flexible than arms 316 such that annuloplasty device 302 takes on a shape controlled by the position of arms 316 and/or collars 326. The expanded configuration of annuloplasty device 302 has an inner diameter ID and an outer diameter OD. Although "diameter" is used to describe a dimension of annuloplasty device 302, in some examples, annuloplasty device 302 is not circular in cross-section and the "diameter" may instead refer to, e.g., a greatest or smallest cross-sectional dimension.

As illustrated in FIG. 3A, anchors 328A and 328B (collectively, "anchors 328") may be deployed from respective arms 316. In some examples, delivery device 300 may include additional anchors and/or anchors having any suitable shape and/or configuration to engage a tissue at a target site. Anchors 328 may engage the tissue at the target site, such as, for example, tissue near an annulus of a mitral valve of a patient, when arms 316 and/or annuloplasty device 302 are in the respective expanded configurations.

After engaging the tissue at the target site when arms 316 and/or annuloplasty device 302 are in the respective expanded configurations, delivery device 300 may be controlled to reduce the inner diameter ID and/or outer diameter OD (the "diameter") of annuloplasty device 302. Reducing the diameter of annuloplasty device 302, when engaged with the tissue at the target site via anchors 328, may cause the tissue to be drawn toward longitudinal axis 314. In examples in which target site includes the annulus of the mitral valve MV of a patient, reducing the diameter of annuloplasty device 302 may reduce a diameter of the annulus of the mitral valve and/or bring the anterior leaflet and posterior leaflet into closer proximity to improve coaption of the leaflets.

For example, collar 332 may be controlled to move in a proximal direction. In response, distal ends 324 of arms 316 may move toward longitudinal axis 314. In this way, collars 326 apply a force to annuloplasty device 302 that results in a reduced inner diameter ID and/or outer diameter OD of annuloplasty device 302 compared to the expanded configuration.

After delivery device 300 is used to reduce the inner diameter ID and/or outer diameter OD of annuloplasty device 302, annuloplasty device 302 may be retained in the reduced ID and/or OD configuration using any suitable technique. For example, additional anchors may be used to hold annuloplasty device 302 in the reduced ID and/or OD configuration.

Additionally, or alternatively, delivery device 300 may include a retainer wire 336 and a lock 338 configured to engage retainer wire 336. In some examples, after controlling collar 332 to reduce the diameter of annuloplasty device 302, delivery device 300 may be controlled to pull taut retainer wire 336 and crimp lock 338 to hold retainer wire 336 in the taut configuration. For example, retainer wire 336 and/or lock 338 may be operatively coupled to a pull wire or an additional catheter (not shown) of delivery device 300. In this way, retainer wire 336 may retain annuloplasty device 302 in a reduced-diameter configuration. In some examples, a force may be applied to ends 340 of retainer wire 336 to at least partially draw annuloplasty device 302 from the expanded configuration of annuloplasty device 302 to the reduced-diameter configuration of annuloplasty device 302.

In some examples, delivery device 300 and other delivery devices described herein are configured to maintain annuloplasty device 302 in an expanded diameter (e.g., OD and/or ID) configuration during implantation in heart 10. With the aid of delivery device 300, a clinician may use anchors 328 to fix the expanded diameter annuloplasty device 302 the annulus or other tissue proximate a heart valve. After delivery device 300 is released from annuloplasty device 302, annuloplasty device 302 may assume a pre-set configuration (e.g., an at rest configuration), which is smaller in diameter than the expanded diameter configuration. In the pre-set configuration, annuloplasty device 302 may apply a radially inward force to the valve annulus, thereby bringing leaflets of the valve closer together, which may improve coaptation of the valve leaflets.

In some examples, a distal end of each respective arm of the plurality of arms of an annuloplasty device delivery device may include a respective releasable hinge assembly coupled to a respective collar. FIGS. 4A-4D are conceptual diagrams illustrating an example delivery device 400 including a releasable hinge assembly 401. Delivery device 400 may be the same as or substantially similar to delivery devices 200 or 300 describe above, except for the differences described herein.

Figure 4A:
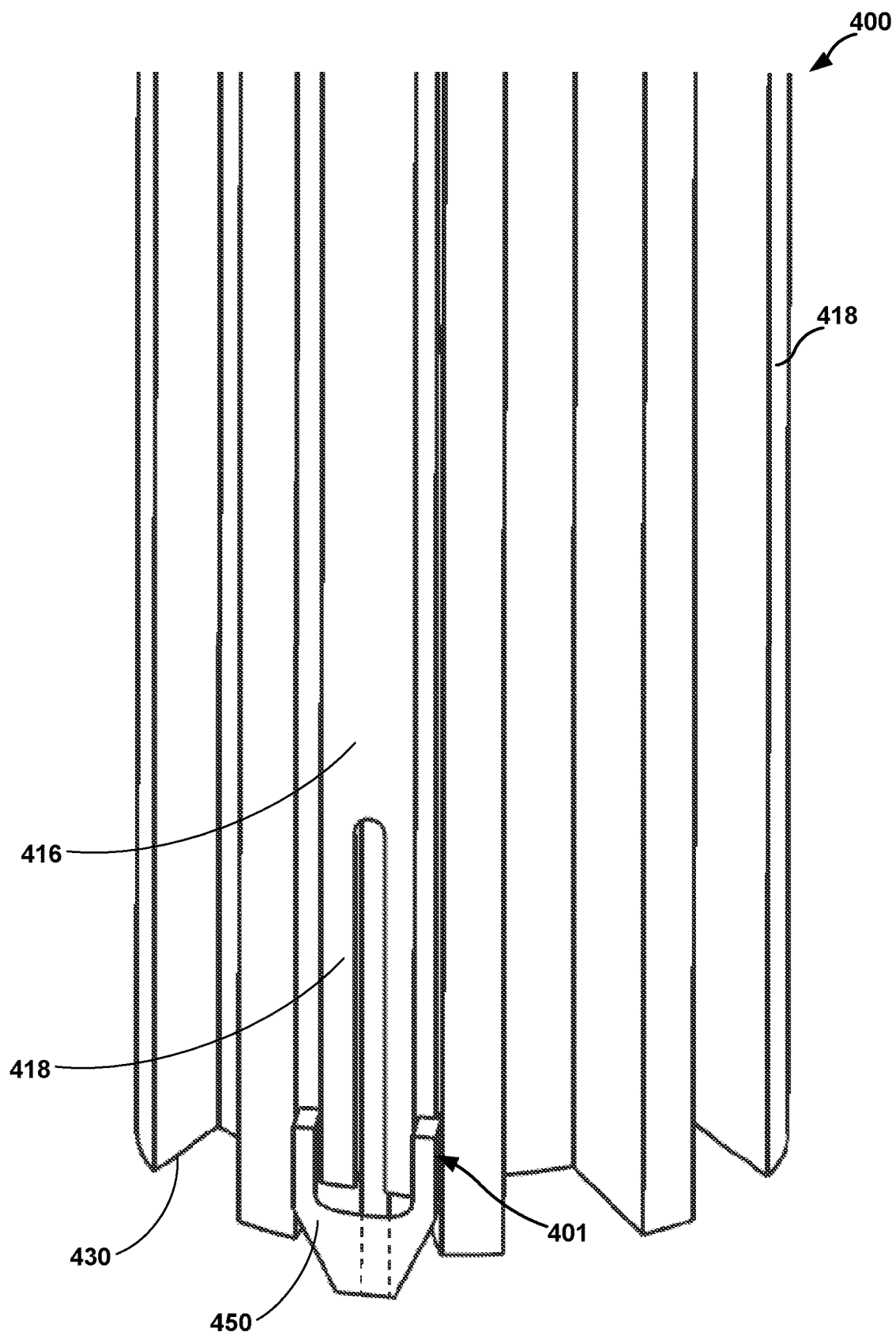
FIGS. 4A-4D are conceptual diagrams illustrating an example delivery device including a releasable hinge assembly.
Figure 4B:
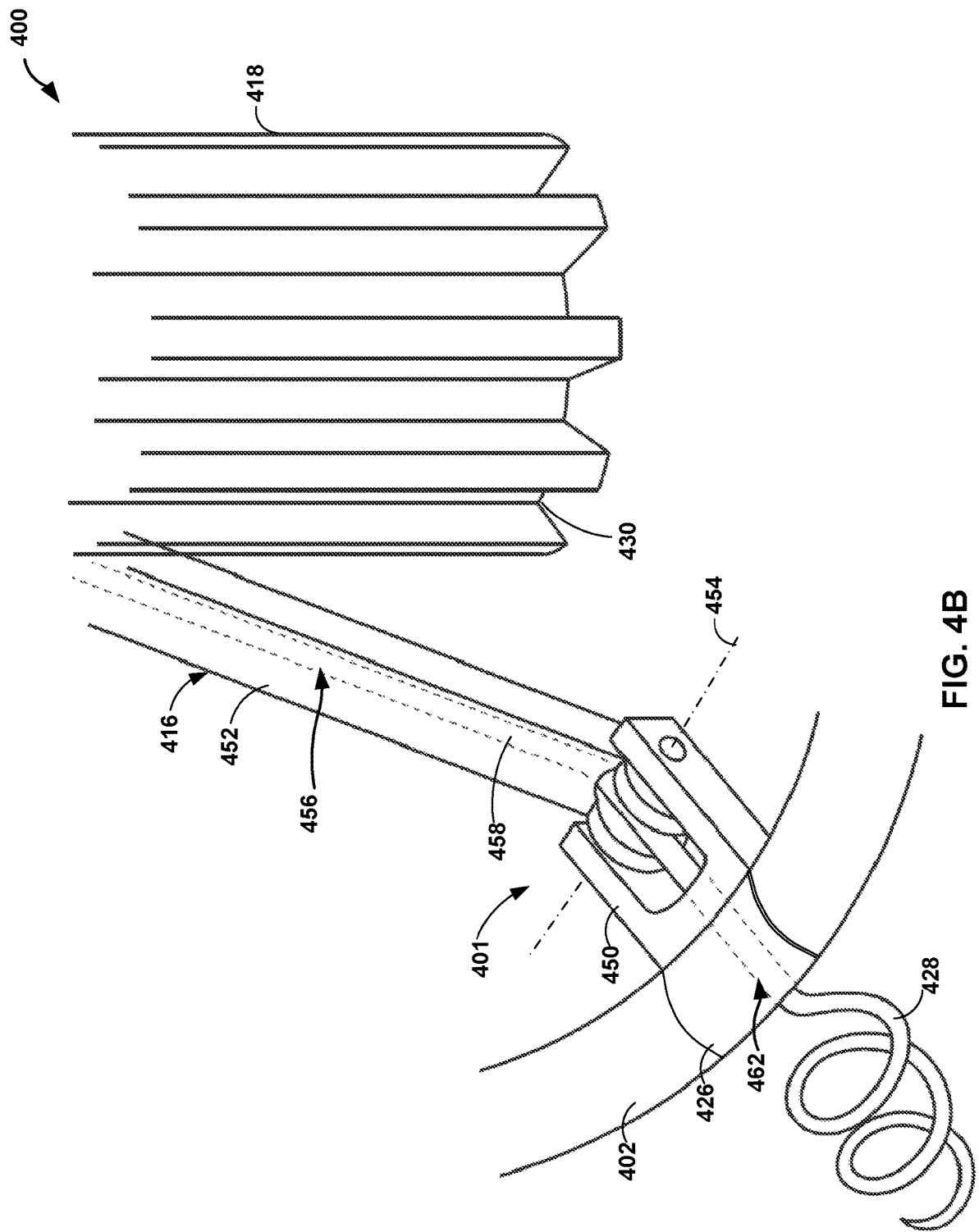

Releasable hinge assembly 401 includes a distal portion 452 of arm 416 and a hinge 450. As illustrated in FIG. 4A, arm 416 may be configured to nest within recess 430 defined by a delivery device 400 when arms 416 are in a retracted configuration. In some examples, as illustrated in FIG. 4B, hinge 450 may be coupled to annuloplasty device 402 via a collar 426. As described above, anchor 428 may be configured to engage tissue at a treatment site to secure annuloplasty device 402 to the treatment site (also referred to herein as a target site).

Figure 4C:
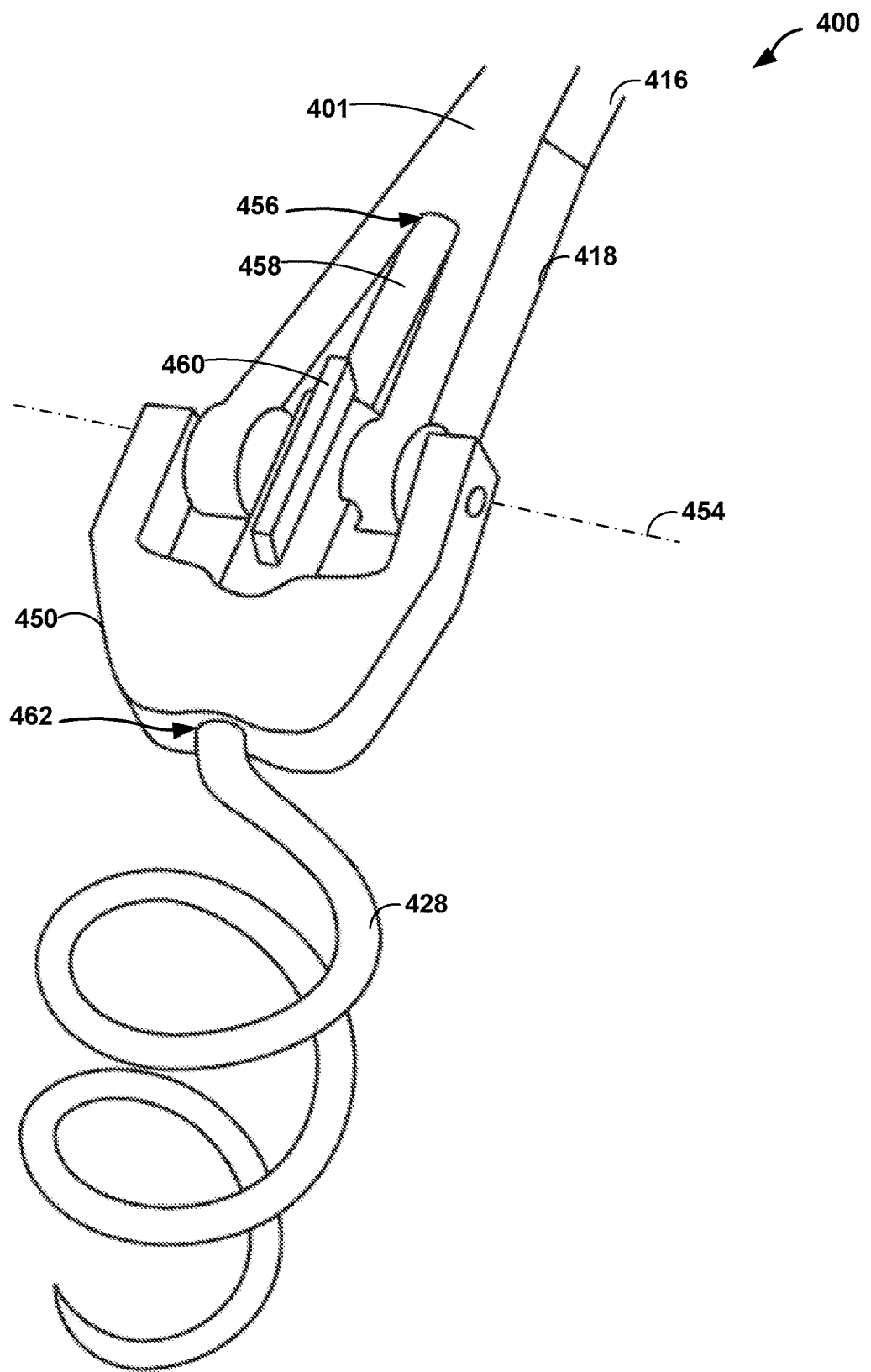
Figure 4D:
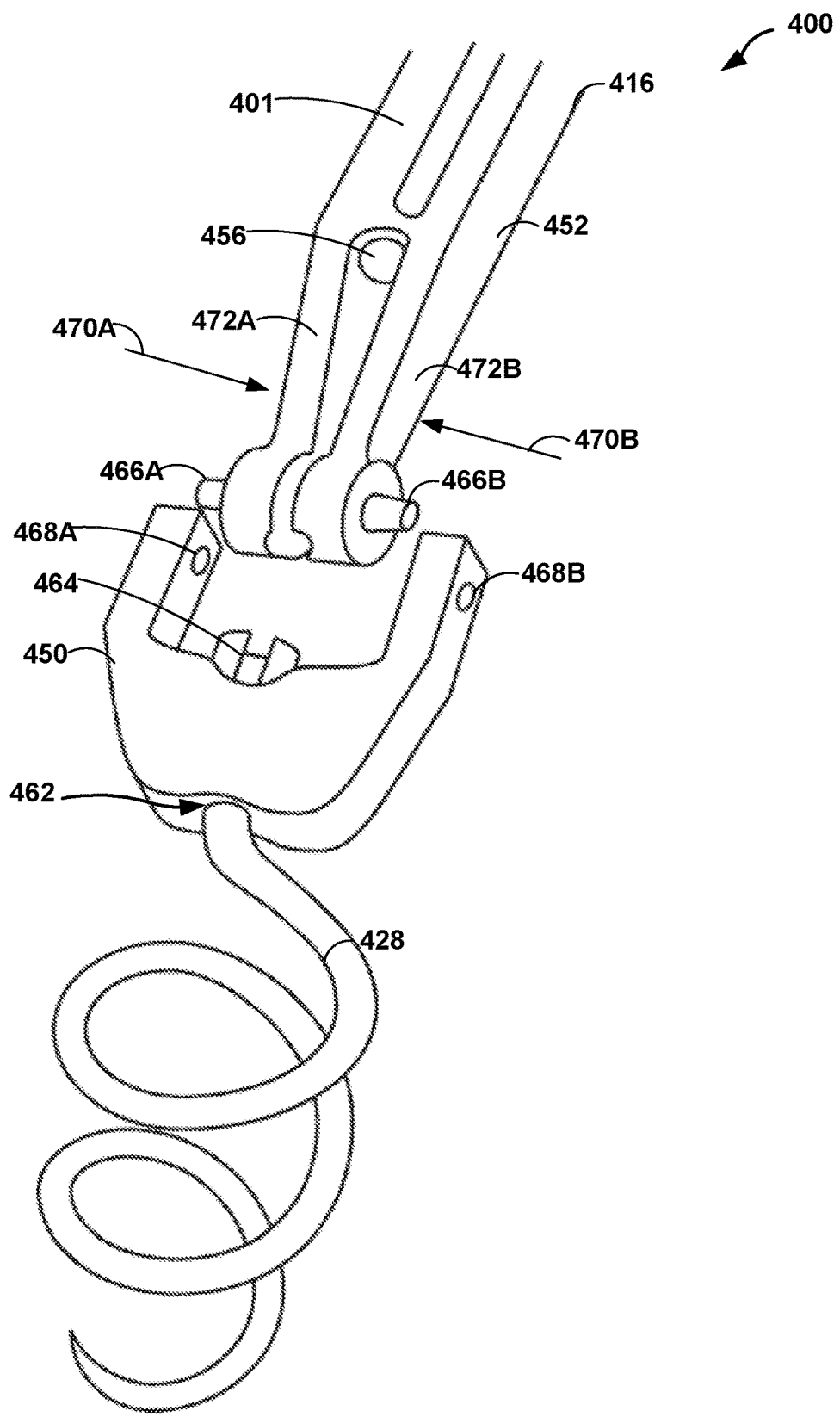

Distal portion 452 of arm 416 and hinge 450 may define any suitable type of hinge, such as a ball and socket joint, a rivet hinge, or the like. In some examples, as best illustrated in FIG. 4D, distal portion 452 may include one or more pins 466A and 466B configured to extending into one or more corresponding apertures 468A and 468B of hinge 450, such that distal portion 452 and hinge 450 may be moveably coupled in a hinge configuration.

As discussed above, anchors 428 may be deployed from arms 416. In an undeployed configuration of anchor 428, as illustrated in FIG. 4A, anchor 428 may be disposed within lumen 456 defined by arm 416. In the undeployed configuration, hinge 450 may be configured to rotate in at least one direction. For example, hinge 450 may rotate about axis 454 (FIGS. 4B and 4C).

In some examples, control wire 458 may be disposed in sliding engagement with lumen 456 and configured to deploy anchor 428. During deployment of anchor 428, control wire 458 may be controlled, e.g., via a control member (e.g., control member 208 shown in FIG. 2) of a handle, to push anchor 428 in a distal direction out of lumen 456. Anchor 428 may pass through lumen 462 of hinge 450. Anti-rotation key 460 may reduce rotation of anchor 428 relative to the respective arm 416 during deployment. Control wire 458 may be configured to push anchor 428 through lumen 462 of hinge 450 until anti-rotation 460 key engages with a keyhole 464 defined by hinge 450, as illustrated in FIG. 4B. Engagement of anti-rotation 460 key with a keyhole 464 may prevent anchor 428 from passing through lumen 462 and/or lock anchor 428 in the deployed configuration. During deployment of anchor 428, anchor 428 and/or control wire 458 may extend through lumens 456 and 462, which may reduce rotation of hinge 450. Reducing rotation of hinge 450 during deployment may improve accuracy of deployment of anchor 528 at a treatment site.

After deployment of anchor 428, control wire 458 may be withdrawn from lumen 462 of hinge 450 such that hinge 450 may rotate. For example, rotation of hinge 450 after deployment of anchor 428 may enable arm 416 to maintain contact of annuloplasty device 402 with tissue at the treatment site as the annuloplasty device 402 is moved from an expanded configuration to a reduced-diameter configuration, as discussed above in reference to FIGS. 3A and 3B. In some examples, distal portion 452 of arm 416 may be configured to disengage with hinge 450 in response to withdrawal of push member 454 into lumen 456. For example, distal portion 452 may include two spring recoil members 472A and 472B configured to retract inward, as indicated by arrows 470A and 470B in FIG. 4D when push member 454 is withdrawn into lumen 456. In this way, arm 16 may be controllably decoupled from hinge 450 after reducing the diameter of annuloplasty device 402.

Figure 5A:
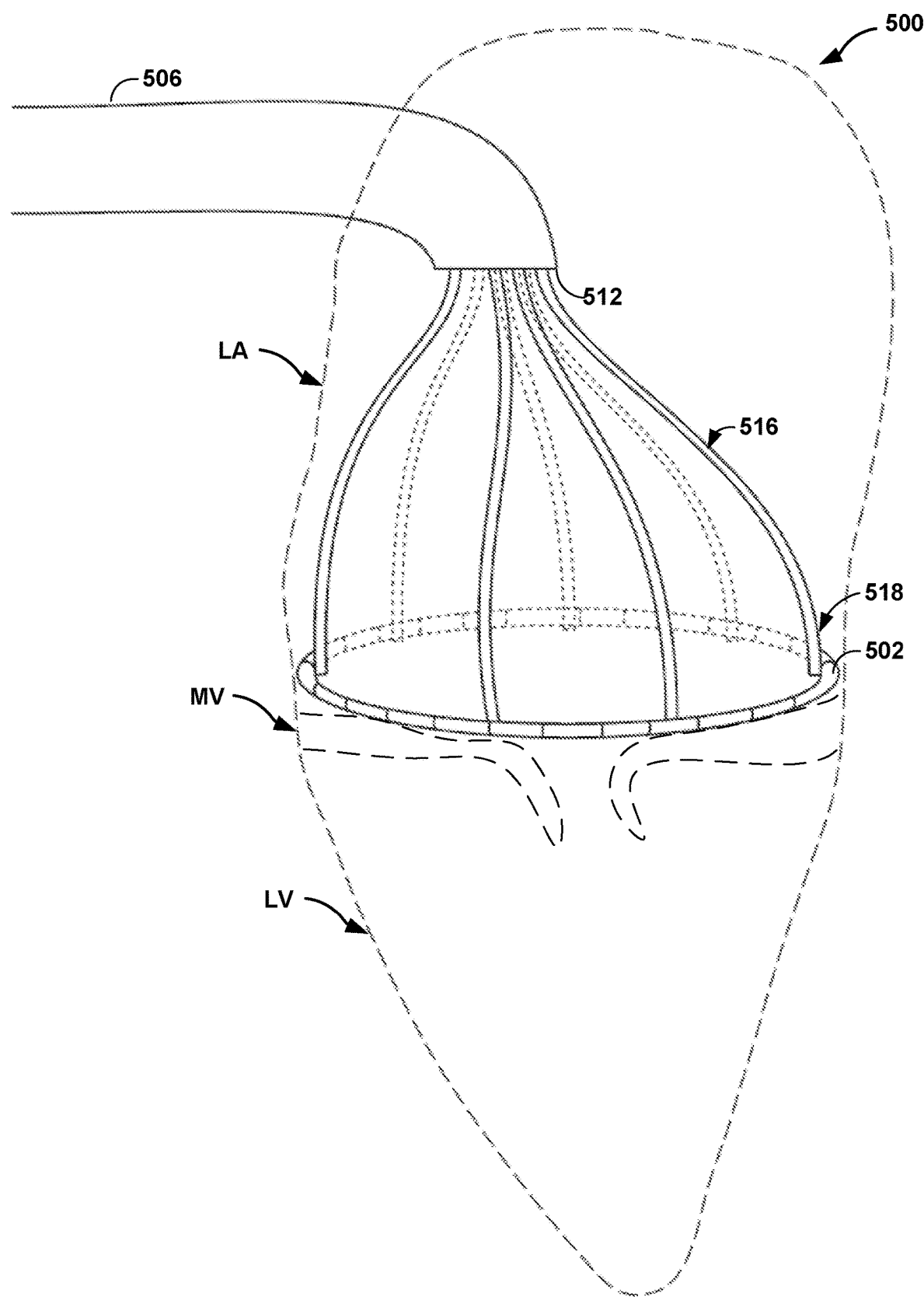
FIGS. 5A and 5B are conceptual diagrams illustrating an example delivery device including a plurality of flexible arms.
Figure 5B:
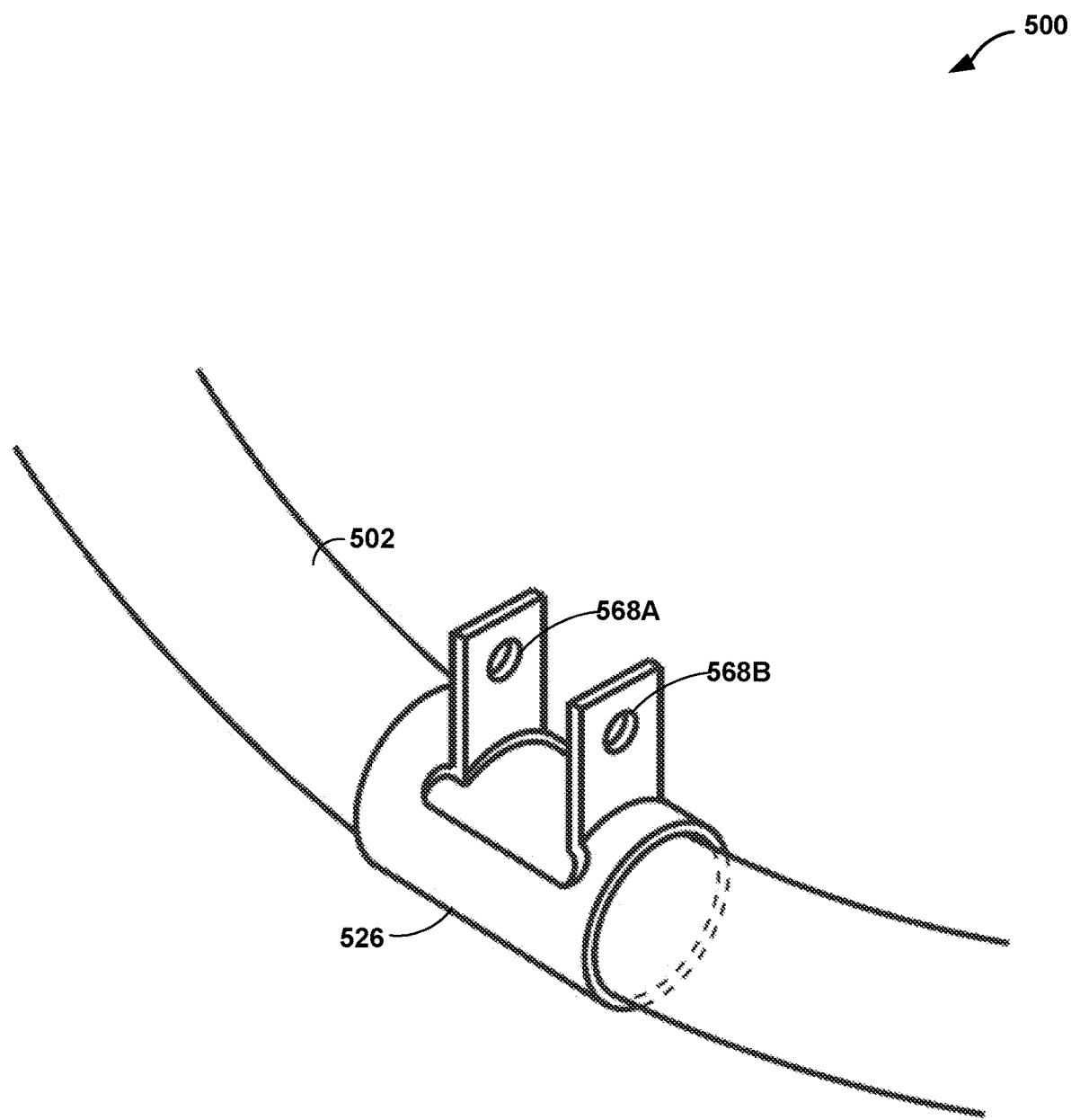

In some example, the arms of a delivery device may be flexible or at least partially flexible. For example, flexible arms may be configured to conform to a shape of tissues at the target site, such as the annulus of the mitral valve MV or walls of the left atrium. FIGS. 5A and 5B are conceptual diagrams illustrating an example delivery device 500 including a plurality of flexible arms 516 ("arms 516"). Delivery device 500 may be the same as or substantially similar to any one or more of delivery devices 200, 300, and 400 describe above, except for the differences describe herein.

In some examples, arms 516 may be configured to have a degree of flexibility sufficient to enable each arm of arms 516 to conform to anatomy of mitral valve MV while still sufficiently rigid to apply a force on annuloplasty device 502 to modify a shape of device 502. For example, arms 516 may be deployed from distal end 512 of elongate body 506. A length of each arm of arms 516 may be individually controllable, for example, at respective control members on a handle (not shown) of delivery device 500. Individually controlling the length of each arm of arms 516 may enable a clinician to modify a shape of annuloplasty device 502 during implantation to conform to the anatomy of mitral valve MV. In some examples, arms 516 may be configured to self-expand into a preformed shape. For example, arms 516 may include a shape-memory alloy, such as a nickel titanium alloy. In some examples, arms 516 may be configured to expand to contact a wall of the left atrium LA, an annulus of mitral valve MV, or both.

In some examples, annuloplasty device 502 may include a flexible fabric body and, as illustrated in FIG. 5B, a plurality of collars 526 ("collars 526") configured to releasably couple to arms 516 of delivery device 500. In some examples, collars 526 may include rigid segments of the flexible fabric body of annuloplasty device 502. In some examples, as illustrated in FIG. 5B, collars 526 may include a rivet hinge. The rivet hinge may be configured to controllably decouple from arms 516, for example, in response to withdrawing a pin coupled to apertures 568A and 568B into a respective arm of arms 516 via a control wire.

As discussed above, delivery device 500 may include a plurality of anchors (not shown). In some examples, the plurality of anchors may be deployed from a lumen of arms 516. In some examples, the plurality of anchors may be disposed on an external surface of arms 516. In examples in which the plurality of anchors is disposed on an external surface of a distal portion 518 of arms 516, each anchor of the plurality of anchors may be configured to be threaded into tissue at a target site via a torqueable shaft releasably coupled to each anchor.

After deployment of the plurality of anchors, one or more of arms 516 may be configured to reduce a diameter of annuloplasty device 502. In some examples, distal end 512 may be advanced distally (e.g., toward mitral valve MV) while arms 516 are pulled taunt to result in a reduction in the diameter of annuloplasty device 502. In some examples, one or more of arms 516 may be configured to pull taunt a retainer wire to reduce a diameter of annuloplasty device 502 and crimp a lock on the retainer wire to hold the retainer wire in the taunt configuration.

Figure 6:
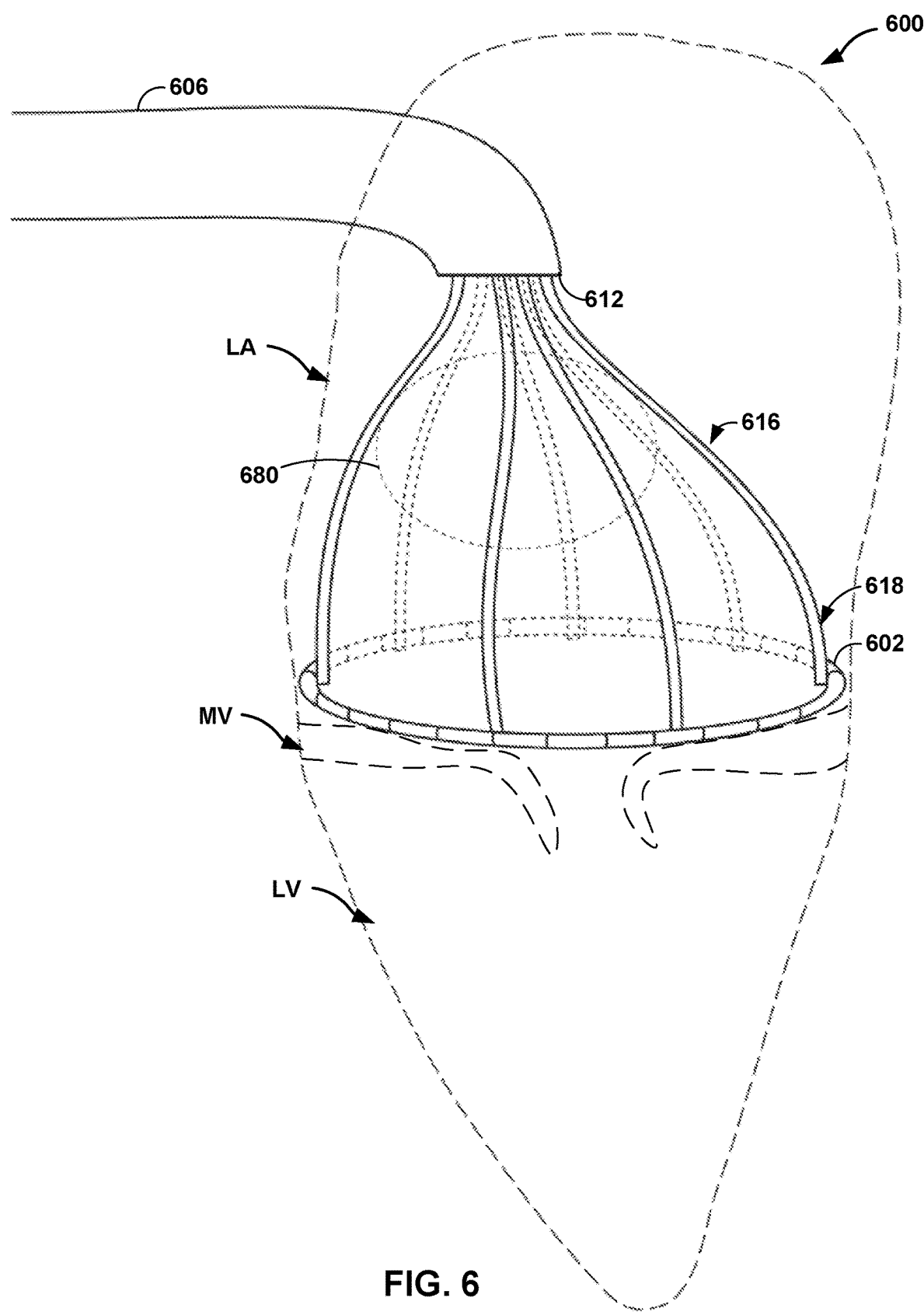
FIG. 6 is a conceptual diagram illustrating an example delivery device including a plurality of flexible arms and an expandable member.

In some examples, an expandable member may be used to control radial forces applied to the arms of a delivery device. FIG. 6 is a conceptual diagram illustrating an example delivery device 600 including a plurality of flexible arms 616 ("arms 616") and an expandable member 680. Delivery device 600 may be the same as or substantially similar to delivery device 500 describe above, except for the differences describe herein. After deploying arms 616 from distal end 612 of elongate body 606, expandable member 680 may be deployed centrally with respect to arms 616. Expandable member 680 may include for example a balloon or similar device configured to be inflated using a fluid, such as saline. Inflation of expandable member 680 may cause arms 616 to move toward the interior walls of left atrium LA. Before, during, or after inflating expandable member 680, the length of each arm of arms 616 may be controlled to position annuloplasty device 602 at a treatment site. In some examples, expandable member 680 may apply a controlled radial force to arms 616 by inflating and/or deflating expandable member 680 such that arms 616 more accurately approach the annulus of mitral valve MV when lengthened. In some examples, the radial force applied by expandable member 680 to area 616 may be greater than a force applied to arms 616 by other means, such as a control wire or manipulation of elongate body 606. In this way, expandable member 680 may improve placement of the annuloplasty device 602 at the annulus of mitral valve MV compared to systems without expandable member 680.

Figure 7:
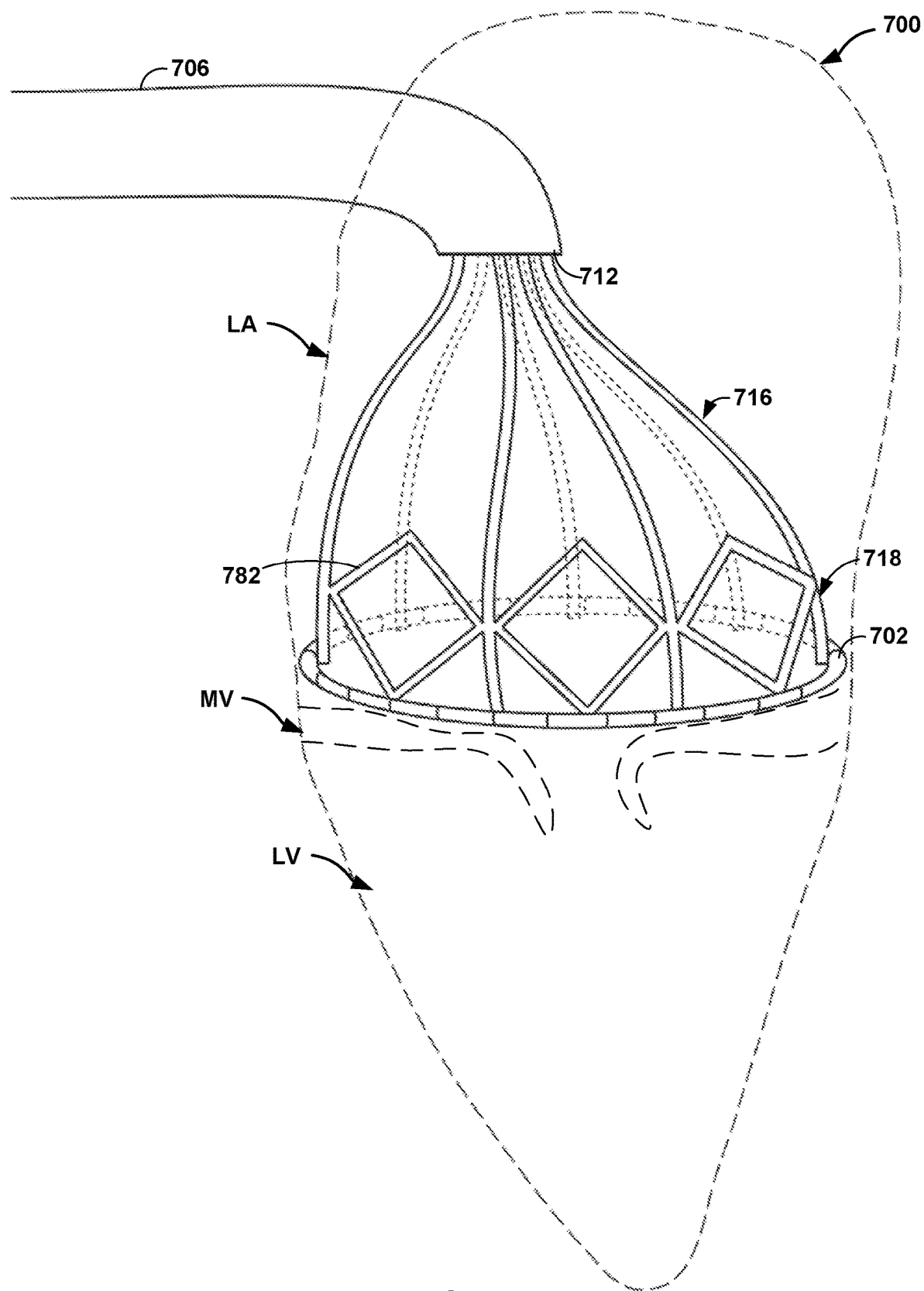
FIG. 7 is a conceptual diagram illustrating an example delivery device including a plurality of flexible arms coupled to a self-expanding structure.

In some examples, a self-expanding structure may be used to control radial forces applied to the arms of a delivery device. FIG. 7 is a conceptual diagram illustrating an example delivery device 700 including a plurality of flexible arms 716 ("arms 716") coupled at joints 718 to a self-expanding structure 782. Delivery device 700 may be the same as or substantially similar to one or more of delivery devices 500 and 600 describe above, except for the differences describe herein. Self-expanding structure 782 may be mechanically coupled to arms 716 and, after deploying arms 716 from distal end 712 of elongate body 706, configured to cause arms 716 to move toward the interior walls of left atrium LA. Self-expanding structure 782 may include a shape-memory material, such as, for example, a nickel titanium alloy. In some examples, self-expanding structure 782 may apply a controlled radial force to arms 716 such that arms 716 more accurately approach the annulus of mitral valve MV when lengthened. In this way, self-expanding structure 782 may improve placement of the annuloplasty device 602 at the annulus of mitral valve MV.

Figure 8A:
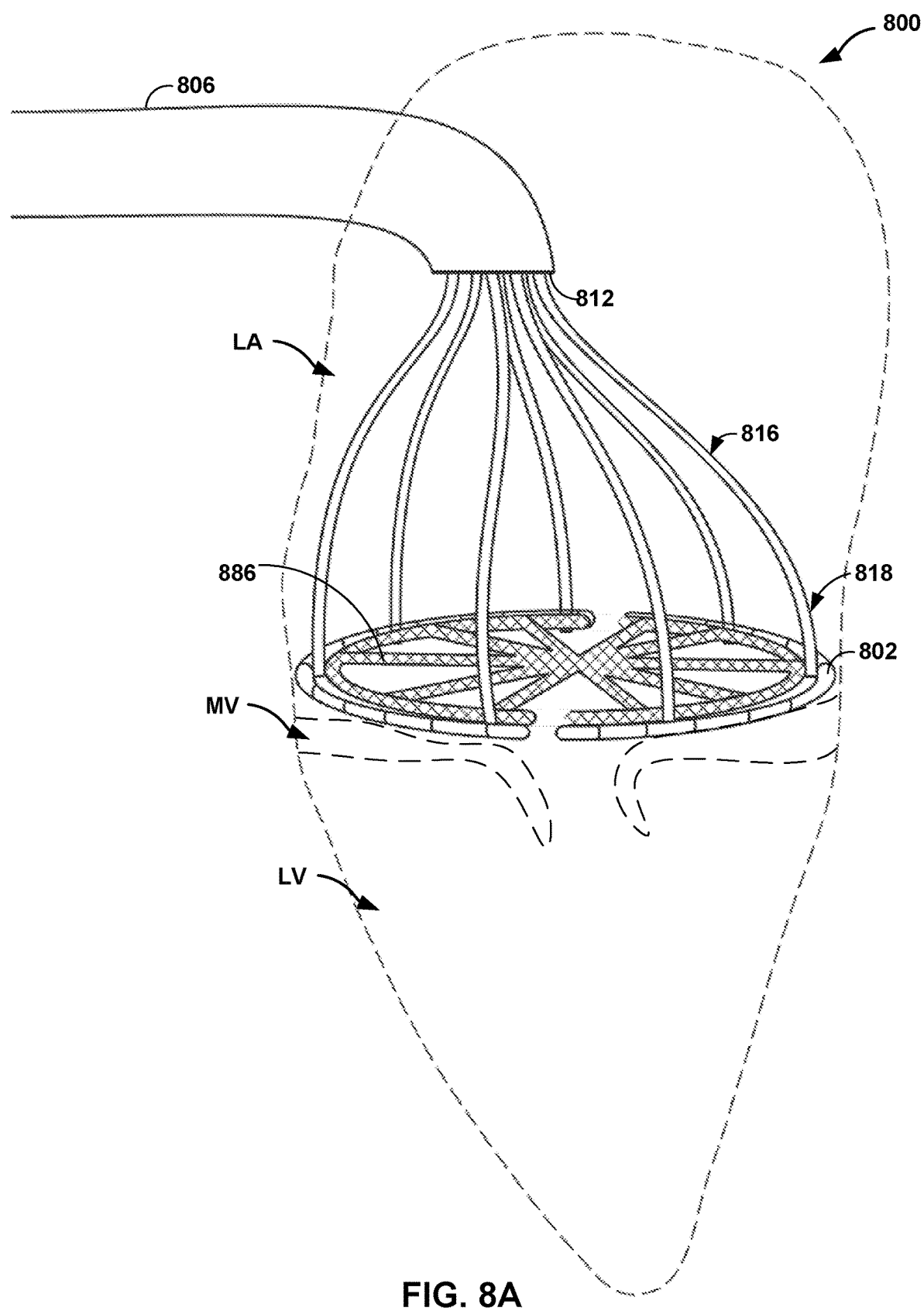
FIGS. 8A and 8B are conceptual diagrams illustrating an example delivery device including a plurality of flexible arms coupled to a self-expanding structure.
Figure 8B:
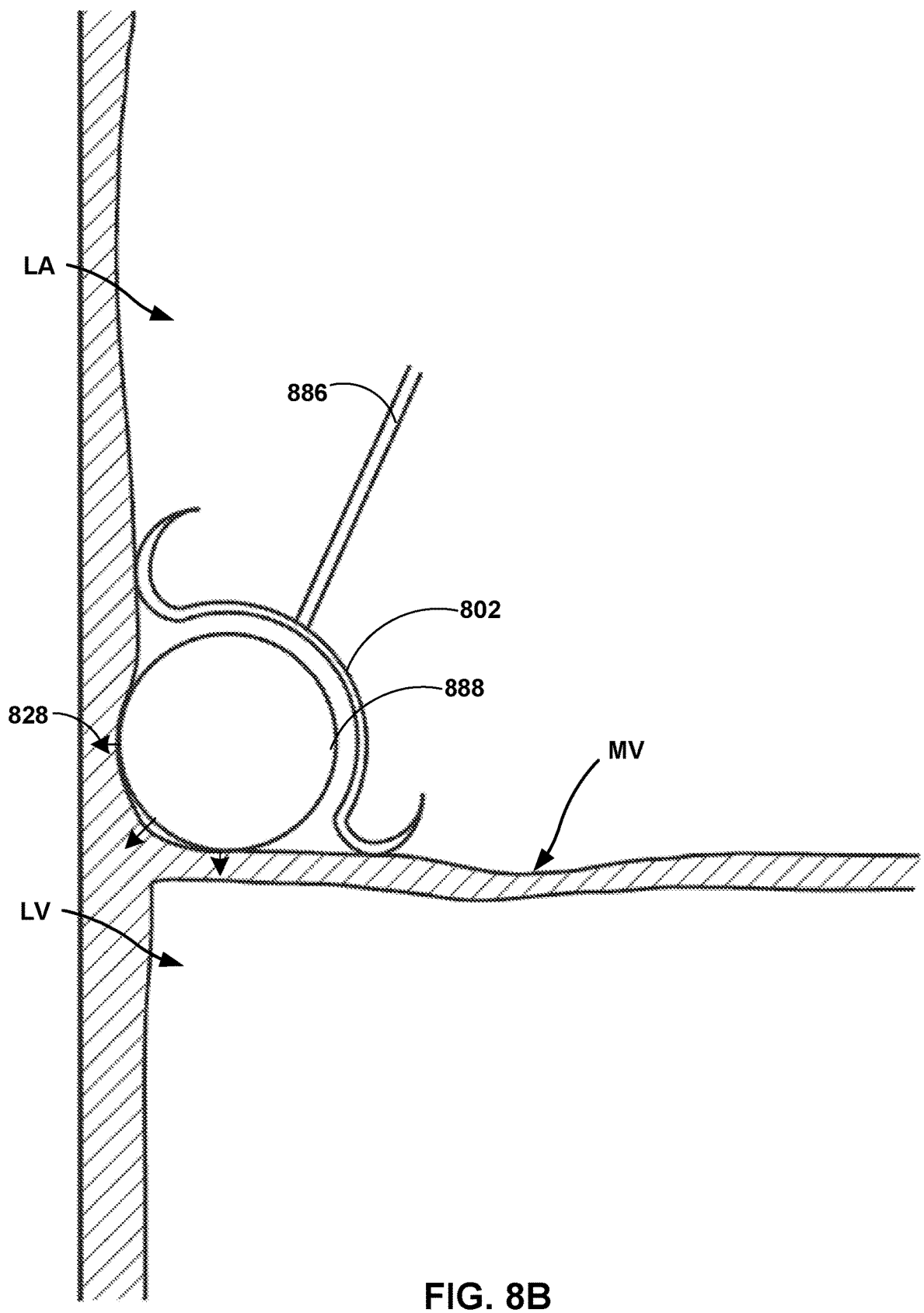

In some examples, a self-expanding structure may be used to control radial forces applied to the arms to push a collapsed or deflated expandable member against the wall of the left atrium. FIGS. 8A and 8B are conceptual diagrams illustrating an example delivery device 800 including a plurality of flexible arms 816 ("arms 816") coupled to a self-expanding structure 886. Delivery device 800 may be the same as or substantially similar to one or more of delivery devices 500, 600, and 700 describe above, except for the differences describe herein. For example, self-expanding structure 886 may include a frame or a radial-spoked wheel including a shape-memory alloy.

After deploying arms 816 from distal end 812 of elongate body 806, self-expanding structure 886 may push a deflated expandable member 888 toward the interior walls of left atrium LA. For example, as illustrated in FIG. 8B, annuloplasty device 802 may include an expandable member 888. In some examples, once in place, expandable member 888 may be inflated in sections, e.g., corresponding to one or more arc segments of annuloplasty device 802. Inflation of each section of expandable member 888 may be configured to cause one or more anchors 828 to deploy and engage with tissue in response to the inflation force. In some examples, expandable member 888 may be inflated with saline. After deploying anchors 828, the diameter of annuloplasty device 802 may be reduced. In some examples, after reducing the diameter of annuloplasty device 802, fast curing polymer may be delivered to expandable member 888 to retain expandable member in the expanded configuration.

The following clauses illustrate example subject matter described herein.

Clause 1. A delivery device comprising: a handle comprising a control member; an elongate body; a plurality of arms extending from a distal portion of the elongate body to a distal collar configured to releasably couple to an annuloplasty device, wherein the plurality of arms is operatively coupled to the control member and configured to position the annuloplasty device at a target site in a patient; and a plurality of anchors configured to secure the annuloplasty device to tissue at the target site, each respective anchor of the plurality of anchors deployable from a respective arm of the plurality of arms.

Clause 2. The delivery device of clause 1, wherein the plurality of arms is configured to controllably reduce a diameter of the annuloplasty device.

Clause 3. The delivery device of clause 1 or 2, further comprising: the annuloplasty device; a retainer wire extending through at least a portion of the annuloplasty device, wherein the retainer wire is configured to controllably reduce a diameter of the annuloplasty device or maintain a reduced diameter of the annuloplasty device; and a lock on the retainer wire configured to maintain the reduced diameter of the annuloplasty device.

Clause 4. The delivery device of any one of clauses 1 through 3, wherein each arm of the plurality of arms is rigid relative to the annuloplasty device.

Clause 5. The delivery device of any one of clauses 1 through 4, wherein each arm of the plurality of arms is flexible.

Clause 6. The delivery device of any one of clauses 1 through 5, wherein the control member comprises a plurality of control members, each respective control member of the plurality of control members coupled to a respective arm of the plurality of arms and configure to control a length of the respective arm extending from the distal portion of the elongate body.

Clause 7. The delivery device of any one of clauses 1 through 6, wherein a proximal end of the plurality of arm is coupled to a collar that is in sliding engagement with the elongate body, wherein a longitudinal position of the collar is controllable by control wire extending from the control member to the collar.

Clause 8. The delivery device of any one of clauses 1 through 7, wherein each respective arm of the plurality of arms defines a lumen through which a respective control wire extends, wherein the respective control wire extends from the control member to a distal portion of the respective arm, wherein the lumen is configured to house a respective anchor in an undeployed configuration, wherein the respective push wire is configured to deploy the respective anchor from the lumen in a distal direction.

Clause 9. The delivery device of any one of clauses 1 through 8, wherein each anchor of the plurality of anchors comprises a shape-memory alloy.

Clause 10. The delivery device of any one of clauses 1 through 9, wherein each respective anchor of the plurality of anchors is configured to assume a helical shape or a hook shape when deployed from a respective arms of the plurality of arms.

Clause 11. The delivery device of any one of clauses 1 through 10, wherein each arm of the plurality of arms comprises a hinge proximal to the distal collar, wherein the hinge is configured to rotate in at least one direction.

Clause 12. The delivery device of any one of clauses 1 through 11, wherein each respective anchor of the plurality of anchors extends through a hinge when in an undeployed configuration such that respective anchor prevents the hinge from rotating, wherein, upon deployment of the respective anchor, the hinge is configured to rotate in at least one direction.

Clause 13. The delivery device of clause 11 or 12, wherein the hinge comprises at least one of a rivet hinge or a ball and socket hinge.

Clause 14. The delivery device of any one of clauses 11 through 13, wherein each respective arm of the plurality of arms comprises a spring recoil member configured to retract inward and disengage from a respective hinge in response to at least one of deployment of a respective anchor in a distal direction or withdrawal of a push member in a proximal direction.

Clause 15. The delivery device of any one of clauses 1 through 14, wherein the tissue comprises a leaflet of a heart valve.

Clause 16. A medical system comprising: an annuloplasty device; and a delivery device configured to deliver the annuloplasty device to a target site in a patient, the delivery device comprising: a handle comprising a control member; an elongate body extending along a longitudinal axis from a proximal end coupled to the handle to a distal portion; a plurality of arms extending from the distal portion of the elongate body to a distal collar configured to releasably couple to the annuloplasty device, wherein the plurality of arms is operatively coupled to the control member and configured to position the annuloplasty device at the target site; and a plurality of anchors configured to secure the annuloplasty device to tissue at the target site, each respective anchor of the plurality of anchors deployable from a respective arm of the plurality of arms.

Clause 17. The medical system of clause 16, wherein the delivery device comprises the delivery device of any one of clauses 2 through 15.

Clause 18. A method comprising: using a delivery device to position an annuloplasty device at a target site in a patient, wherein the delivery device comprises the delivery device of any one of clauses 1 through 15; deploying at least one anchor of the plurality of anchors to secure the annuloplasty device to tissue at the target site; and after deploying the at least one anchor, modifying a shape or a size of the annuloplasty device.

Clause 19. The method of clause 18, wherein modifying the shape or the size of the annuloplasty device comprises: shorting a wire extending through at least a portion of the annuloplasty device to reduce a diameter of the annuloplasty device; and crimping or otherwise fixing the wire to maintain the reduced diameter of the annuloplasty device.

Clause 20. The method of clause 18, wherein modifying the shape or the size of the annuloplasty device comprises releasing the annuloplasty device from the delivery device, wherein the annuloplasty device is configured to assume a pre-set configuration upon release from the delivery device.

Clause 21. The method of clause 18, wherein modifying the shape or the size of the annuloplasty device comprises moving the arms of the delivery device while the arms are connected to the annuloplasty device.

Clause 22. A method of using forming the delivery device of any one of clauses 1 through 15 or the medical system of clause 16 or 17.

Various examples have been described. Any combination of the described systems, devices, operations, or functions is contemplated. These and other examples are within the scope of the following claims.

What is claimed is:

1. A system comprising:
an annuloplasty device; and
a delivery device comprising:
  a handle comprising a control member;
  an elongate body;
  a plurality of arms extending from a distal portion of the elongate body to a distal collar releasably coupled to the annuloplasty device, wherein the plurality of arms is operatively coupled to the control member and configured to position the annuloplasty device at a target site in a patient;
  a plurality of anchors configured to secure the annuloplasty device to tissue at the target site, each respective anchor of the plurality of anchors deployable from a respective arm of the plurality of arms,
  wherein the plurality of arms are relatively rigid and are configured such that the control member moves the plurality of arms to reduce a diameter of the annuloplasty device with the plurality of anchors secured to the tissue at the target site.

2. The system of claim 1, further comprising:
a retainer wire extending through at least a portion of the annuloplasty device; and
a lock on the retainer wire, wherein the retainer wire and the lock are configured to maintain the reduced diameter of the annuloplasty device.

3. The system of claim 1, wherein a proximal end of the plurality of arms is coupled to a proximal collar that is in sliding engagement with the elongate body, wherein a longitudinal position of the proximal collar is configured to be controlled by a control wire extending from the control member to the proximal collar.

4. The system of claim 1, wherein each respective arm of the plurality of arms defines a lumen through which a corresponding control wire extends, wherein the corresponding control wire extends from the control member to a distal portion of the respective arm, wherein the lumen is configured to house a corresponding anchor in an undeployed configuration, wherein the corresponding control wire is configured to deploy the corresponding anchor from the lumen in a distal direction.

5. The system of claim 1, wherein each anchor of the plurality of anchors comprises a shape-memory alloy.

6. The system of claim 1, wherein each respective anchor of the plurality of anchors is configured to assume a helical shape or a hook shape when deployed from a respective arm of the plurality of arms.

7. The system of claim 1, wherein each arm of the plurality of arms comprises a hinge proximal to the distal collar, wherein the hinge is configured to rotate in at least one direction.

8. The system of claim 7, wherein each respective anchor of the plurality of anchors extends through the hinge when in an undeployed configuration such that respective anchor prevents the hinge from rotating, wherein, upon deployment of the respective anchor, the hinge is configured to rotate in the at least one direction.

9. The system of claim 7, wherein the hinge comprises at least one of a rivet hinge or a ball and socket hinge.

10. The system of claim 7, wherein each respective arm of the plurality of arms comprises a spring recoil member configured to retract inward and disengage from a respective hinge in response to at least one of deployment of a respective anchor in a distal direction or withdrawal of a push member in a proximal direction.

11. The system of claim 1, wherein the tissue comprises a leaflet of a heart valve.

12. A medical system comprising:
an annuloplasty device; and
a delivery device configured to deliver the annuloplasty device to a target site in a patient, the delivery device comprising:
  a handle comprising a control member;
  an elongate body extending along a longitudinal axis from a proximal end coupled to the handle to a distal portion;
  a plurality of flexible arms extending from the distal portion of the elongate body to a distal collar configured to releasably couple to the annuloplasty device, wherein the plurality of flexible arms is operatively coupled to the control member and configured to position the annuloplasty device at the target site; and a plurality of anchors configured to secure the annuloplasty device to tissue at the target site, each respective anchor of the plurality of anchors deployable from a respective arm of the plurality of arms;

wherein the plurality of flexible arms is configured to reduce a diameter of the annuloplasty device by maintaining the plurality of flexible arms taut while advancing the distal portion of the elongate member.

13. The system of claim 12, wherein the control member comprises a plurality of control members, each respective control member of the plurality of control members coupled to a respective arm of the plurality of flexible arms and configured to control a length of the respective arm extending from the distal portion of the elongate body.

14. The system of claim 12, wherein the distal collar comprises a rivet hinge.

15. The system of claim 12, further comprising a self-expanding structure coupled to at least some of the arms of the plurality of flexible arms, wherein the self-expanding structure is configured to radially expand the plurality of flexible arms.

16. A method comprising:
using a delivery device to position an annuloplasty device in a radially expanded configuration at a target site in a patient, wherein the delivery device comprises:
a handle comprising a control member;
an elongate body;
a plurality of arms extending from a distal portion of the elongate body to a distal collar configured to releasably couple to the annuloplasty device, wherein the plurality of arms is operatively coupled to the control member and configured to position the annuloplasty device at the target site in a patient; and
a plurality of anchors configured to secure the annuloplasty device to tissue at the target site, each respective anchor of the plurality of anchors deployable from a respective arm of the plurality of arms;
deploying at least one anchor of the plurality of anchors to secure the annuloplasty device to tissue at the target site; and
after deploying the at least one anchor, reducing a diameter of the annuloplasty device by releasing the annuloplasty device from the delivery device, wherein upon release from the delivery device the annuloplasty device assumes a pre-set configuration smaller than the radially expanded configuration.

* * * * *